(12) United States Patent
Kozlowski et al.

(10) Patent No.: US 8,383,380 B2
(45) Date of Patent: *Feb. 26, 2013

(54) SEGMENTED POLYMERS AND THEIR CONJUGATES

(75) Inventors: Antoni Kozlowski, Huntsville, AL (US); Xiaoming Shen, Madison, AL (US); Michael D. Bentley, Huntsville, AL (US); Zhihao Fang, Madison, AL (US); Tony L. Sander, Madison, AL (US)

(73) Assignee: Nektar Therapeutics, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/267,619

(22) Filed: Oct. 6, 2011

(65) Prior Publication Data

US 2012/0027714 A1   Feb. 2, 2012

Related U.S. Application Data

(60) Continuation of application No. 12/898,687, filed on Oct. 5, 2010, now Pat. No. 8,084,572, which is a continuation of application No. 11/402,350, filed on Apr. 11, 2006, now Pat. No. 7,834,138, which is a division of application No. 10/734,858, filed on Dec. 11, 2003, now Pat. No. 7,053,150, which is a continuation-in-part of application No. 10/024,357, filed on Dec. 18, 2001, now Pat. No. 6,774,180.

(60) Provisional application No. 60/256,801, filed on Dec. 18, 2000.

(51) Int. Cl.
*C12N 9/96* (2006.01)

(52) U.S. Cl. ....... 435/188; 424/94.3; 435/180; 435/181; 525/54.1

(58) Field of Classification Search .................. 528/425, 528/271; 424/193.1, 194.1; 435/180, 181, 435/188; 525/54.1
See application file for complete search history.

(56) References Cited

U.S. PATENT DOCUMENTS

| | | | |
|---|---|---|---|
| 4,670,417 A | 6/1987 | Iwasaki et al. |
| 5,252,714 A | 10/1993 | Harris et al. |
| 5,281,698 A | 1/1994 | Nitecki |
| 5,468,478 A | 11/1995 | Saifer et al. |
| 5,650,234 A | 7/1997 | Dolence et al. |
| 5,672,662 A | 9/1997 | Harris et al. |
| 5,824,784 A | 10/1998 | Kinstler et al. |
| 5,900,461 A | 5/1999 | Harris |
| 5,932,462 A | 8/1999 | Harris et al. |
| 6,046,305 A | 4/2000 | Choi |
| 6,348,558 B1 | 2/2002 | Harris et al. |
| 6,413,507 B1 | 7/2002 | Bentley et al. |
| 6,495,659 B2 | 12/2002 | Bentley et al. |
| 6,774,180 B2 | 8/2004 | Kozlowski et al. |
| 7,053,150 B2 | 5/2006 | Kozlowski et al. |
| 7,834,138 B2 | 11/2010 | Kozlowski et al. |
| 2006/0194940 A1 | 8/2006 | Kozlowski |
| 2011/0021761 A1 | 1/2011 | Kozlowski et al. |

FOREIGN PATENT DOCUMENTS

| | | |
|---|---|---|
| JP | 8-59818 | 3/1996 |
| WO | WO 95/11924 | 5/1995 |
| WO | WO 99/29759 | 6/1999 |
| WO | WO 99/45964 | 9/1999 |
| WO | WO 01/26692 | 4/2001 |

OTHER PUBLICATIONS

Abuchowski, et al., "Cancer Therapy with Chemically Modified Enzymes. I. Antitumor Properties of Polyethylene Glycol-Asparaginase Conjugates," Cancer Biochem. Biophys, 7:175-186 (1984).
Andresz, et al., Makromol. Chem., 179:301-312 (1978).
Beauchamp, et al., "A New Procedure for Synthesis of Polyethylene Glycol-Protein Adducts; Effects on Function, Receptor Recognition, and Clearance of Superoxide Dismutase, Lactoferrin, and $\alpha2$-Macroglobulin," Analytical Biochemistry, 131:25-33 (1983).
Brinkley, "A brief survey of methods for preparing protein conjugates with dyes, haptens, and cross-linking reagents," Bioconjug. Chem, 3:2-13 (1992).
Buckman, et al., "Functionalization of Poly(ethylene glycol) and Monomethoxy-Poly(ethylene glycol)," Makromol. Chem., 182:1379-1384 (1981).
Choi, et al., "Star-Shaped Poly(Ether-Ester) Block Copolymers: Synthesis, Characterization, and Their Physical Properties", Macromolecules, vol. 31, pp. 8766-8774, (1998).
Duncan, et al., "A new reagent which may be used to introduce sulfhydryl groups into proteins, and its use in the preparation of conjugates for immunoassay", Anal. Biochem. 132(1):68-73 (1983).
Elling, et al., "Immunoaffinity Partitioning: Synthesis and Use of Polyethylene Glycol-Oxirane for Coupling to Bovine Serum Albumin and Monoclonal Antibodies," Biotechnology and Applied Biochemistry, 13:354-362 (1991).
Goodson, et al., "Site-Directed PEGylation of Recombinant Interleukin-2 at its Glycosylation Site," Bio/Technology, 8(4):343-346 (1990).
Greenwald, et al., "Highly Water Soluble Taxol Derivatives: 7-Polyethylene Glycol Carbamates and Carbonates," J. Org. Chem., 60:331-336 (1995).
Harris, et al., "Synthesis and Characterization of Poly(ethylene glycol) Derivatives," J. Polym. Sci. Schem. Ed., 22:341-352 (1984).
Ishizu, et al., "Synthesis of Functional Star-Shaped Poly(ethylene Oxide) Using the Macromonomer Technique", Macromol. Rapid Commun., vol. 21, pp. 979-982, (2000).
Joppich, et al., "Synthesis of Glycyl-L-tryptophylglycine Substituted by Poly(ethylene oxide) at both the Carboxy and the Amino End Groups," Makromol. Chem., 180:1381-1384 (1979).

(Continued)

*Primary Examiner* — Gregory Listvoyb
(74) *Attorney, Agent, or Firm* — Timothy A. Marquart

(57) ABSTRACT

Segmented water soluble polymers, containing a higher molecular weight segment linked to a lower molecular weight segment, are described. In one embodiment, the polymer segments are poly(ethylene glycol) segments. The segmented polymers are functionalized and are useful for conjugation to various moieties such as pharmacologically active substances. Also described are conjugates of such polymers and methods of their preparation.

22 Claims, No Drawings

OTHER PUBLICATIONS

Kogan, "The Synthesis of Substituted Methoxy-Poly(ethylene glycol) Derivatives Suitable for Selective Protein Modification," Synthetic Communications, 22(16):2417-2424 (1992).
Mattson, et al., "A practical approach to crosslinking," Mol. Biol. Rep. 17(3):167-183 (1993).
Means, et al., "Chemical modifications of proteins: history and applications," Bioconjug. Chem. 1:2-12 (1990).
Okamoto, et al., "Kinetic Study on Reactions Between Polymer Chain-Ends—II. Reactions Between Chlorosulphonyl-Ended and Primary Amino-Ended Polyoxyethylenes Followed by Fluorometry," Eur. Polym J., 19(4):341-346 (1983).
Olson, et al., "Preparation and Characterization of Poly(ethylene glycol)ylated Human Growth Hormone Antagonist," Chemistry and Biological Applications, pp. 170-181 (1997).
Pitha, et al., "Detergents Linked to Polysaccharides" Preparation and Effects on Membranes and Cells, Eur. J. Biochem., 94:11-18 (1979).
Romani, et al., "Synthesis of Unsymmetrical Cystine Peptides: Directed Disulfide Pairing with the Sulfenohydrazide Method," Chemistry of Peptides and Proteins, 2:29-34 (1984).
Sartore, et al., "Enzyme Modification by MPEG with an Amino Acid or Peptide as Spacer Arms," Applied Biochemistry and Biotechnology, 27:45-54 (1991).
Sawhney, et al., "Bioerodible Hydrogels Based on Photopolymerized Poly(ethylene glycol)-co-poly($\alpha$-hydroxy acid) Diacrylate Macromers," Macromolecules, 26:581-587 (1993).
Tondelli, et al., "Poly(ethylene Glycol) Imidazolyl Formates as Oligomeric Drug-Binding Matrices," Journal of Controlled Release, 1:251-257 (1985).
Veronese, et al., "Activation of Monomethoxy-Polyethylene Glycols by Phenylchloroformates and Modification of Ribonuclease and Superoxide Dismutase," Applied Biochemistry and Biotechnology, 11:141-152 (1985).
Woghiren, et al., "Protected Thiol-Polyethylene Glycol: A New Activated Polymer for Reversible Protein Modification," Bioconjugate Chem., 4:314-318 (1993).
Wong, et al., "Chemical crosslinking and the stabilization of proteins and enzymes," Enzyme Microb. Technol. 14:866-874 (1992).
Zalipsky, et al., "Attachment of Drugs to Polyethylene Glycols," Eur. Polym. J., 19(12):1177-1183 (1983).
Zalipsky, "Chemistry of polyethylene glycol conjugates with biologically active molecules," Advanced Drug Delivery Reviews, 16:157-182 (1995).
Enzon Pharmaceuticals, Macromolecular Engineering Technologies, pp. 1-14, (2004).
NEKTAR™—Transforming Therapeutics, Nektar Molecule Engineering: Polyethylene Glycol and Derivatives for Advanced PEGylation, pp. 1-20, Catalog—2003, (Jul. 2003).
NEKTAR™—Transforming Therapeutics, Nektar Advanced PEGylation: Polyethylene Glycol and Derivatives for Advanced PEGylation, pp. 1-24, Catalog—2004, (Jul. 2004).
NEKTAR™—Transforming Therapeutics, Nektar Advanced PEGylation: Polyethylene Glycol and Derivatives for Advanced PEGylation, pp. 1-30, (Catalog 2005-2006).
NOF Corporation, "PEG Derivatives, Phospholipid and Drug Delivery Materials for Pharmaceuticals", pp. 1-46, Catalogue 2003-1st, (Jan. 2003).
NOF Corporation, "PEG Derivatives, Phospholipid and Drug Delivery Materials for Pharmaceuticals", pp. 1-50, Catalogue 2003-2nd, (Mar. 2004).
NOF Corporation, "PEG Derivatives, Phospholipids and Drug Delivery Materials for Pharmaceutical Products and Formulations", pp. 1-59, Catalogue Ver. 8, (Apr. 2006).
Polypure, Products; PEG amines; PEG acids and amino acids; PEG thiols and disulfides; Biotins, (Apr. 2004).
Polypure, Products; PEG amines; PEG acids and amino acids; PEG thiols and disulfides; BIOTINS, (Apr. 2005).
Quanta Biodesign, Labeling, Derivatization and Crosslinking Reagents for Biological and Related Materials with dPEG™, pp. 1-38, (Mar. 12, 2004).
Quanta Biodesign, Labeling, Modification and Crosslinking Reagents incorporating our unique monodispersed dPEG™ Technology, pp. 1-31, (Nov. 5, 2004).
Quanta Biodesign, Ltd., Leading innovator, producer and provider of monodisperse discrete PEG™ (dPEG™) derivatives, (Product Catalog), pp. 1-51, (Updated: Jul. 18, 2005).
Quanta Biodesign, Ltd., Leading innovator, producer and provider of monodisperse discrete PEG™ (dPEG™) derivatives, (Product Catalog), pp. 1-51, (Updated: Nov. 17, 2005).
Shearwater Polymers, Inc., Polyethylene Glycol and Derivatives, pp. 1-49, (Catalog—Mar. 1995).
Shearwater Polymers, Inc., Polyethylene Glycol and Derivatives, pp. 1-53, (Catalog—Jul. 1997).
Shearwater Polymers, Inc., Polyethylene Glycol and Derivatives: Functionalized Biocompatible Polymers for Research and Pharmaceuticals, pp. 1-50, (Catalog—Jan. 2000).
Shearwater Corporation, Polyethylene Glycol and Derivatives for Biomedical Applications, pp. 1-17, (Catalog—Jul. 2001).
PCT International Search Report corresponding to PCT/US2001/049081 date of mailing Jul. 18, 2002.
PCT Written Opinion corresponding to PCT/US2001/049081 date of mailing Sep. 9, 2002.
PCT International Preliminary Examination Report corresponding to PCT/US2001/049081 date of mailing Apr. 14, 2003.
Australian Examiner's First Report corresponding to Australian Patent Application No. 2002246705 dated Sep. 7, 2005.
Canadian Examination Report corresponding to Canadian Patent Application No. 2,431,977 dated May 5, 2009.
Canadian Examination Report corresponding to Canadian Patent Application No. 2,431,977 dated Oct. 23, 2009.
European Communication corresponding to European Patent Application No. 01994295.2 dated Jul. 7, 2005.
European Communication corresponding to European Patent Application No. 01994295.2 dated Mar. 15, 2006.
European Communication of a notice of opposition corresponding to European Patent Application No. 01994295.2 dated Feb. 7, 2008.
European Summons to attend oral proceedings corresponding to European Patent Application No. 01994295.2 dated Feb. 25, 2010.
Korean Notice of Grounds for Rejection corresponding to Korean Patent Application No. 2003-7008077 issuance date Sep. 20, 2006.
Korean Notice of Grounds for Rejection corresponding to Korean Patent Application No. 2003-7008077 issuance date Dec. 28, 2006.
Korean Notice of Grounds for Rejection corresponding to Korean Patent Application No. 2003-7008077 issuance date Jun. 7, 2007.
Decision rejecting the opposition, corresponding to European Patent Application No. 01 994 295.2-2102 / 1345982, dated Jan. 31, 2011.
Pre-Action Notification of Reexamination, corresponding to Taiwanese Patent Application No. 090131261, dated Oct. 2003.

SEGMENTED POLYMERS AND THEIR CONJUGATES

CROSS REFERENCE TO RELATED APPLICATIONS

This application is a continuation of U.S. Ser. No. 12/898,687, filed Oct. 5, 2010, now U.S. Pat. No. 8,084,572, which is a continuation of 11/402,350, filed Apr. 11, 2006, now U.S. Pat. No. 7,834,138, which is a divisional of U.S. Ser. No. 10/734,858, filed Dec. 11, 2003, now U.S. Pat. No. 7,053,150, which is a continuation-in-part of U.S. Ser. No. 10/024,357, filed Dec. 18, 2001, now U.S. Pat. No. 6,774,180, which claims the benefit of provisional application U.S. Ser. No. 60/256,801, filed Dec. 18, 2000, all of which are hereby incorporated by reference in their entireties.

FIELD OF THE INVENTION

The invention relates to medium to high molecular weight, functionalized, water soluble polymers useful for conjugation to various moieties, including pharmacologically active substances. In particular, the invention relates to functionalized water soluble polymers, such as poly(ethylene glycols), containing a higher molecular weight segment linked to a lower molecular weight segment, and methods of their preparation.

REFERENCES

Brinkley, M. A brief survey of methods for preparing protein conjugates with dyes, haptens, and cross-linking reagents. *Bioconjug. Chem.* 3:2-13 (1992).

Carlsson, J., Drevin, H., and Axen, R. Protein thiolation and reversible protein-protein conjugation. N-Succinimidyl 3-(2-pyridyldithio)propionate, a new heterobifunctional reagent. *Biochem. J.* 173(3):723-737 (1978).

Duncan, R. J., Weston, P. D., Wrigglesworth, R. A new reagent which may be used to introduce sulfhydryl groups into proteins, and its use in the preparation of conjugates for immunoassay. *Anal. Biochem.* 132(1):68-73 (1983).

Eyzaguirro, J. CHEMICAL MODIFICATION OF ENZYMES: ACTIVE SITE STUDIES. John Wiley & Sons, New York (1987).

Hope, M. J., Bally, M. B., Webb, G. and Cullis, P. R. Production of large unilamellar vesicles by a rapid extrusion procedure. Characterization of size distribution, trapped volume and ability to maintain a membrane potential. *Biochim. Biophys. Acta.* 812:55-65 (1985).

Mattson, G., Conklin, E., Desai, S., Nielander, G., Savage, M. D. and Morgensen, S. A practical approach to crosslinking. *Mol. Biol. Rep.* 17(3):167-183 (1993).

Means, G. E. and Feeney, R. E. Chemical modifications of proteins: history and applications. *Bioconjug. Chem.* 1:2-12 (1990).

Wong, S. H. CHEMISTRY OF PROTEIN CONJUGATION AND CROSS-LINKING. CRC Press, Boca Raton, Fla. (1991).

Wong, S. S. and Wong, L. J. Chemical crosslinking and the stabilization of proteins and enzymes. *Enzyme Microb. Technol.* 14:866-874 (1992).

BACKGROUND OF THE INVENTION

Scientists and clinicians face a number of challenges in development of therapeutically active agents into forms suitable for delivery to a patient. For example, pharmaceutically useful biomolecules, including antibodies and antibody fragments, can now be prepared on a useful scale, due to advances in biotechnology, but the clinical usefulness of potentially therapeutic biomolecules is often hampered by their rapid proteolytic degradation, their instability upon manufacture, storage or administration, and/or their immunogenicity. Therapeutically potent molecules can be hampered by low aqueous solubility; paclitaxel (Taxol™) is one significant example.

Conjugation of active agents to water-soluble polymers has been found to reduce immunogenicity and antigenicity, as well as increasing half-life in circulation, as a result of decreased clearance and/or decreased enzymatic degradation in systemic circulation. The frequency of administration can thus be reduced, which is particularly beneficial in the large number of cases in which the agent is administered by injection. As a further benefit, active agents that are only marginally soluble in water often demonstrate a significant increase in water solubility when conjugated to a water soluble polymer.

Polyethylene glycol, due to its documented safety and its approval by the FDA for both topical and internal use, has been conjugated to a variety of active agents. Such a conjugated active agent is conventionally referred to as "PEGylated." Commercially successful PEGylated active agents include PEGASYS® PEGylated interferon α-2a (Hoffmann-La Roche, Nutley, N.J.), PEG-INTRON® PEGylated interferon α-2b (Schering Corp., Kennilworth, N.J.), NEULASTA™ PEG-filgrastim (Amgen Inc., Thousand Oaks, Calif.) and SOMAVERT® pegvisomant, a PEGylated human growth hormone receptor antagonist (Pfizer, New York, N.Y.). Non-peptidic small molecules such as fluorouracil (Ouchi et al., *Drug Des. Discov.* 9(1):93-105, 1992) have also been prepared in PEGylated form.

In view of these promising features, there has been an increasing need for high purity functionalized derivatives of PEG and other water soluble polymers having medium to high molecular weight. However, the synthesis of such compounds is often complicated by the difficulty in removing polymeric impurities that accumulate during multi-step preparations. For example, end-capped (i.e., nominally monofunctional) polyethylene glycol starting material often contains significant amounts of PEG diol impurity, ranging from 0.5% to over 30% by weight. The diol impurity, and especially its reaction products when carried through a series of synthetic transformations, can be extremely difficult to analyze and remove. Higher molecular weight polymeric side-products, in particular, are generally quite difficult to remove and require time-consuming and expensive chromatographic techniques. Accordingly, there remains a need in the art for improved methods of preparing functionalized derivatives of water soluble polymers such as PEG.

SUMMARY OF THE INVENTION

The invention provides segmented, functionalized water soluble polymer derivatives and methods of their preparation. In one aspect, the invention provides a water soluble polymer, where the polymer comprises:

(i) a first water soluble polymer segment having at least 4 and at most about 2000 monomeric units (designated "POLY$_A$");

(ii) a second water soluble segment comprising 1 to about 120 monomeric units (designated "POLY$_B$"), which has a lower molecular weight than that of POLY$_A$ and is covalently attached to POLY$_A$ through a linkage X, as described further below; and (iii) a functional group, Y, attached to POLY$_A$ or POLY$_B$. A functional group may be located on either one or both of POLY$_B$ and POLY$_A$. Typically, a functional group is located on POLY$_B$.

Typically, $POLY_B$ has fewer monomeric units, as well as a lower molecular weight, than $POLY_A$. The molecular weight of the $POLY_A$ segment is preferably at least two times, and more preferably at least four times, that of the $POLY_B$ segment (excluding functional groups). The molecular weight of the $POLY_A$ segment may also be at least ten or at least twenty times that of the $POLY_B$ segment (excluding functional groups).

Each of the water soluble segments designated $POLY_A$ and $POLY_B$ independently comprises one monomer, or up to three different monomers, selected from the group consisting of alkylene glycol, olefinic alcohol, vinyl pyrrolidone, hydroxyalkyl methacrylamide, hydroxyalkyl methacrylate, saccharide, α-hydroxy acid, phosphazene, oxazoline, and N-acryloylmorpholine. That is, each segment is, independently, a homopolymer of one monomer selected from this group, a binary copolymer comprising two different monomers selected from this group, or a terpolymer comprising three different monomers selected from this group; homopolymers and binary copolymers are generally preferred. The different monomers may be of the same monomer type; for example, two alkylene glycols, such as ethylene glycol and propylene glycol. Preferably, $POLY_A$ and $POLY_B$ have the same monomeric composition, with the possible exception of attached functional groups and/or capping groups.

In selected embodiments, each of $POLY_A$ and $POLY_B$ is independently a poly(alkylene glycol). For example, each of $POLY_A$ and $POLY_B$ may be selected from poly(ethylene glycol) and an ethylene glycol/propylene glycol copolymer. In preferred embodiments, each of $POLY_A$ and $POLY_B$ is a poly(ethylene glycol).

$POLY_A$ may be a "high" molecular weight segment, i.e. having more than 200 monomeric repeating units, or a "medium" molecular weight segment, i.e. having 4 to about 200 monomeric repeating units. In selected embodiments, a "high molecular weight" $POLY_A$ segment has at least 200, 250, 500, 1000, 1500, or 2000 or more monomeric units. These ranges correspond, for example, to poly(ethylene glycol) segments having molecular weights of at least about 8800, 11,000, 22,000, 44,000, 66,000, or 88,000 or more Daltons, respectively.

In other selected embodiments, $POLY_A$ is a "medium" molecular weight segment having at least 10, 20, 25, 50, 100, 125, 150, or 175 monomeric units, up to about 200 monomeric units. These ranges correspond, for example, to poly(ethylene glycol) segments having molecular weights of at least about 440, 880, 1100, 2200, 4400, 5500, 6600, and 7700 Daltons, respectively, up to about 8800 Daltons.

In selected embodiments of segmented PEG-based polymers, where each of $POLY_A$ and $POLY_B$ is a poly(ethylene glycol) segment, $POLY_A$ has a medium molecular weight range selected from about 200-5000, about 500-2000, and about 1000-1500. In other embodiments of PEG-based segmented polymers, $POLY_A$ has a high molecular weight range selected from about 8800 to about 20000, about 15000 to about 50000, and about 20000 to about 90000.

Preferably, the segment $POLY_B$ has at least two monomeric units; more preferably, $POLY_B$ has at least three monomeric units. In other preferred embodiments, $POLY_B$ has at most about 100, and more preferably at most 50, monomeric units. In selected embodiments, $POLY_B$ has 2, 3, 4, 5, 10, 15, 25, 35, 45, 75 or 100 monomeric units. These ranges correspond, for example, to poly(ethylene glycol) segments having molecular weights of about 88, 132, 176, 220, 440, 660, 1100, 1540, 1980, 3300, and 4400 Daltons, respectively.

In selected embodiments of segmented PEG-based polymers, where each of $POLY_A$ and $POLY_B$ is a poly(ethylene glycol) segment, $POLY_B$ preferably has a molecular weight range selected from 44 to about 4400, 44 to about 1500, 220 to about 2000, and about 2000 to about 3300.

The linkage X between the polymer segments is distinct from the monomeric units of the polymer segments; that is, there is a clear delineation between the structure of the linkage and the structure of the adjacent portions of the polymer segments. In selected embodiments, X comprises an amide, a carbamate, a carbonate, a urea, an ester, an amine, a thioether, or a disulfide; in further selected embodiments, X comprises an amide, a carbonate, or a carbamate. The linkage is typically formed by reaction between functional groups on precursor segments, as described further below. The linkage may also comprise spacer groups, as described further below.

The functional group Y preferably comprises a moiety selected from hydroxyl, amine, hydrazine, hydrazide, thiol (nucleophilic groups), carboxylic acid, carboxylic ester, including imide ester, orthoester, carbonate, isocyanate, isothiocyanate, aldehyde, ketone, thione, alkenyl, acrylate, methacrylate, acrylamide, sulfone, maleimide, disulfide, iodo, epoxy, sulfonate, thiosulfonate, silane, alkoxysilane, halosilane, and phosphoramidate. More specific examples of these groups include succinimidyl ester or carbonate, imidazolyl ester or carbonate, benzotriazole ester or carbonate, p-nitrophenyl carbonate, vinyl sulfone, chloroethylsulfone, vinylpyridine, pyridyl disulfide, iodoacetamide, glyoxal, dione, mesylate, tosylate, and tresylate. Also included are other activated carboxylic acid derivatives, as well as hydrates or protected derivatives of any of the above moieties (e.g. aldehyde hydrate, hemiacetal, acetal, ketone hydrate, hemiketal, ketal, thioketal, thioacetal). Preferred electrophilic groups include succinimidyl carbonate, succinimidyl ester, maleimide, benzotriazole carbonate, glycidyl ether, imidazoyl ester, p-nitrophenyl carbonate, acrylate, tresylate, aldehyde, and orthopyridyl disulfide.

When Y is a nucleophile, preferred nucleophiles include amine, hydrazine, hydrazide (i.e. —C(═O)NHNH$_2$) and thiol, particularly amine.

Particular structural embodiments of Y, where the functional group may be attached to an alkyl spacer group, include structures of the form —(CH$_2$)$_r$CO$_2$Q, where Q is selected from N-succinimide, N-sulfosuccinimide, N-phthalimide, N-glutarimide, N-tetrahydrophthalimide, N-norbornene-2,3-dicarboximide, benzotriazole, 7-azabenzotriazole, and imidazole. Also included are groups of the form —(CH$_2$)$_r$CH(OR)$_2$, —(CH$_2$)$_r$CHO, —(CH$_2$)$_r$NH$_2$, and —(CH$_2$)$_r$M, where M is N-maleimide. In these structures, r is 0-5, preferably 1-5, and more preferably 2-3.

In selected embodiments of the segmented polymer, the functional group Y comprises an amine or protected amine, and is preferably present on $POLY_B$, and the linkage X comprises a carbamate, an amide, a urea, or a carbonate. In further preferred embodiments of this group, each of $POLY_A$ and $POLY_B$ is independently a poly(ethylene glycol). In various embodiments, $POLY_A$ has a molecular weight of about 200 to 40,000, 200 to 10,000, or 200-1000; in one embodiment, $POLY_A$ has a molecular weight of about 1000. Preferably, $POLY_A$ is end-capped with a C$_1$-C$_{20}$ alkoxy group, more preferably with a C$_1$-C$_{12}$ alkoxy group, e.g. a methoxy group.

In one embodiment, the segmented polymer is linear (i.e., each of $POLY_A$ and $POLY_B$ is linear) and comprises a functional group at each terminus. The functional groups may be the same (homobifunctional) or different (heterobifunctional). Alternatively, the segmented polymer is linear and comprises a functional group at one terminus, e.g. on $POLY_B$, and a capping group, such as alkoxy, on the other terminus. Such polymers are referred to herein as "monofunctional".

In a further embodiment, the segmented polymer comprises two POLY$_B$ segments and has the structure Y-POLY B-X-POLY A-X-POLY B-Y, where each X and each Y is independently selected, and X and Y are as defined above. In a preferred embodiment, each X in the structure above is the same and each Y is the same.

In preferred embodiments, the invention provides a conjugate formed by attachment of one or more pharmacologically active agents to the above-described polymer, typically via the functional group(s) Y. The agent(s) may include, for example, proteins, peptides, carbohydrates, oligonucleotides, DNA, RNA, lipids, or small molecule compounds, as discussed further below.

In further embodiments, each of POLY$_A$ or POLY$_B$ may be hydrolytically or enzymatically degradable, in that each segment independently comprises at least one hydrolytically or enzymatically degradable linkage separating monomeric units of the polymer segment. Alternatively, or in addition, the linkage(s) joining POLY$_A$ and POLY$_B$ segments may be hydrolytically or enzymatically degradable.

Each of POLY$_A$ and POLY$_B$ may be independently selected from the group consisting of linear, branched, forked, multi-armed, and dendrimeric polymer segments, as defined further below. The segmented polymer comprising POLY$_A$ and POLY$_B$ may also have an architecture selected from linear, branched, forked, multi-armed, and dendrimeric.

For example, the polymer may be a linear polymer, having the general structure

POLY$_A$-X-POLY$_B$-Y    (Ia)

or

POLY$_B$-X-POLY$_A$-Y    (Ib)

where structure Ia is generally preferred. In further selected embodiments, a linear segmented PEG polymer is provided, having the structure:

R—(CH$_2$CH$_2$O)$_n$—CH$_2$CH$_2$—X—(CH$_2$CH$_2$O)$_m$—CH$_2$CH$_2$—Y    (Ic)

where:
R is a functional group or capping group;
n is at least 4 and at most about 2000,
m is between 1 and about 120, where m<n,
X is a linking group, as described herein, and
Y is a functional group, as described herein, which may be the same or different from R when R is a functional group. In selected embodiments, n is at most about 1000, at most about 500, or at most about 200.

When R is a capping group, it is preferably selected from C$_1$-C$_{20}$ alkoxy or aryloxy, more preferably C$_1$-C$_{10}$ alkoxy or aryloxy, and a phospholipid. In further selected embodiments, R is C$_1$-C$_5$ alkoxy or benzyloxy. A preferred phospholipid is a dialkyl phosphatidylethanolamine, such as distearoyl phosphatidylethanolamine (DSPE). The terminal amine of the head group may be used to link the lipid to the PEG chain via, for example, a carbamate linkage.

Alternatively, the polymer may be a branched polymer, having a general structure selected from (POLY$_A$-X-POLY$_B$)$_p$-L-Y    (IIa)

(POLY$_A$-X)$_p$-L-POLY$_B$-Y    (IIb)

and (POLY$_A$)$_p$-L-X-POLY$_B$-Y    (IIc)

where POLY$_A$, POLY$_B$, X, and Y are as defined above; L represents a branched spacer group; and p is $\geq 2$, preferably 2 to about 100, more preferably 2 to about 10. In one embodiment, p is 2.

Preferably, the branch point in the branched spacer group L comprises a carbon atom (—CH<), though it may also comprise a nitrogen atom (—N<). The branch point is linked to adjacent moieties, such as X, Y or a polymer segment, directly or by chains of atoms of defined length. Each chain of atoms may comprise, for example, alkyl, ether, ester, or amide linkages, or combinations thereof.

In selected embodiments of structures IIa-c above, the POLY$_A$ segment is a PEG segment (PEG$_A$) comprising at least 4 and at most about 2000 —CH$_2$CH$_2$O— monomeric units; X is selected from an amide, a carbamate, a carbonate, an ester, a urea, an amine, a thioether, and a disulfide; and the POLY$_B$ segment is a PEG segment (PEG$_B$) comprising at least 1, preferably at least 2, and at most about 120 —CH$_2$CH$_2$O— monomeric units, with the proviso that PEG$_B$ has a lower molecular weight than that of PEG$_A$. Preferred ranges of p include 1-100, 2-20, and 2-10.

Also provided are "forked" polymers, in which a single segmented polymer (which can itself be, for example, linear or branched) is linked to two functional groups, or, in a conjugate, to two pharmacologically active agents, as in the following general structures:

POLY$_A$-L-(X-POLY$_B$-Y)$_q$    (IIIa)

POLY$_A$-X-L-(POLY$_B$-Y)$_q$    (IIIb)

POLY$_A$-X-POLY$_B$-L-(Y)$_q$    (IIIc)

where POLY$_A$, POLY$_B$, X, and Y are as defined above; L represents a branched spacer group; and q is $\geq 2$, preferably 2 to about 100, more preferably 2 to about 10. In one embodiment, q is 2. Preferably, the branch point in the spacer group comprises a carbon atom (>CH—), though it may also comprise a nitrogen atom (>N—). A "multiarmed" polymer of the invention comprises three or more water-soluble polymer chains attached to a central core structure, and can be represented by the general structure:

M-{POLY$_A$-X-(POLY$_B$-Y)$_q$}$_x$    (IV)

where M is a core structure, having several linkage points for attachment of POLY$_A$. The value of x is typically 3 to about 100, more typically 3 to about 20. The core structure M is preferably selected from a polyol, a polyamine, and an amino acid whose side chain bears a functional group, and more preferably selected from a polyol and a polyamine.

In selected embodiments of structure (IV), q is 1 or 2; that is, each "arm" represents a linear polymer (q=1) or a "forked" polymer (q=2). In further embodiments, x is 3 to 20, or 3 to 10. Generally, q is 1, such that each POLY$_A$ is linked to a single POLY$_B$. However, q can be greater than 1, and POLY$_B$ can include more than one Y or a polyfunctional Y, as noted above. Where q is >1 or POLY$_B$ includes more than one Y, branched spacer groups, as represented by L above, are incorporated as appropriate. Generally, POLY$_B$ includes a single group Y.

The multiarmed polymer may also include some POLY$_A$ segments which are not further substituted. Accordingly, structure (IV) can represent a branched or dendritic polymer segment in which each of a plurality of POLY$_A$ polymer arms (where the plurality is equal to or less than q) is covalently attached to a POLY$_B$-Y segment via a covalent linkage, X.

In selected embodiments, the multiarmed polymer is a PEG polymer, e.g.:

(IV')

where $PEG_A$ represents poly(ethylene glycol) comprising at least 4 and at most about 2000 —$CH_2CH_2O$— monomeric units, and $PEG_B$ represents poly(ethylene glycol) comprising at least 1 and at most about 120 —$CH_2CH_2O$— monomeric units, with the proviso that $PEG_B$ has a lower molecular weight than that of $PEG_A$. In selected embodiments, X comprises a carbamate, an amide, a carbonate, an ester, a urea, an amine, a thioether, or a disulfide. Preferably, X comprises a carbamate, an amide, a urea, or a carbonate.

The invention also provides gels, also referred to as hydrogels, which may be crosslinked or uncrosslinked, comprising a water soluble, segmented polymer as described above.

In another aspect, the invention provides a method of forming a water-soluble polymer comprising two or more segments, as described above. The method comprises reacting a first water soluble polymer segment, having at least 4 and at most about 2000 monomeric units, and having at least one first functional group, Z, with a second water soluble segment, having from 1 to about 120 monomeric units and having at least one second functional group, Y', thereby covalently bonding the first and second segments by reaction of Z with Y'. Either the first or second segment, preferably the second segment, further comprises an additional functional group, Y, that is not readily reactive with either Z or Y'.

The second segment has a lower molecular weight than the first segment, as described for $POLY_B$ and $POLY_A$ above. As also described for $POLY_A$ and $POLY_B$ above, each of the first and second segments independently comprises up to three different monomers which are selected from the group consisting of alkylene glycol, olefinic alcohol, vinylpyrrolidone, hydroxyalkylmethacrylamide, hydroxyalkytmethacrylate, saccharides, α-hydroxy acid, vinyl alcohol, polyphosphazene, polyoxazoline, and N-acryloylmorpholine.

Selected embodiments of size and molecular weight for the first and second segments are also as described for $POLY_A$ and $POLY_B$ above. In preferred embodiments, each of the first and second segments is a poly(alkylene glycol), such as PEG. In one embodiment, the first polymer segment is a linear methoxypoly(ethylene glycol).

Preferably, each of the reacting groups Z and Y' independently comprises a group selected from hydroxy, thiol, amine, hydrazide, hydrazide, N-succinimidyl carbonate, succinimidyl ester, benzotriazole carbonate, glycidyl ether, imidazolyl ester, aldehyde, maleimide, ortho-pyridyl disulfide, acrylate, and vinyl sulfone. The groups are generally selected such that one is nucleophilic (e.g. hydroxy, thiol, amine, hydrazide) and the other is electrophilic.

The remaining functional group Y preferably comprises a moiety selected from hydroxyl, amine, hydrazine, hydrazide, thiol (nucleophilic groups), carboxylic acid, carboxylic ester, imide ester, orthoester, carbonate, isocyanate, isothiocyanate, aldehyde, ketone, thione, alkenyl, acrylate, methacrylate, acrylamide, sulfone, maleimide, disulfide, iodo, epoxy, sulfonate, thiosulfonate, silane, halosilane, and phosphoramidate. More specific examples of these groups include succinimidyl ester or carbonate, imidazoyl ester or carbonate, benzotriazole ester or carbonate, vinyl sulfone, chloroethylsulfone, vinylpyridine, pyridyl disulfide, iodoacetamide, glyoxal, dione, mesylate, tosylate, and tresylate. Also included are various activated carboxylic acid derivatives, as well as hydrates or protected derivatives of any of the above moieties (e.g. aldehyde hydrate, hemiacetal, acetal, ketone hydrate, hemiketal, ketal, thioketal, thioacetal). Preferred electrophilic groups include succinimidyl carbonate, succinimidyl ester, maleimide, benzotriazole carbonate, glycidyl ether, imidazoyl ester, p-nitrophenyl carbonate, acrylate, aldehyde, and orthopyridyl disulfide. When Y is a nucleophile, preferred nucleophiles include amine, hydrazine, hydrazide, and thiol, particularly amine. The group Y may be present in protected form, particularly as required to prevent reaction with Z or Y'.

The method may further comprises the step of conjugating a pharmacologically active agent to the segmented polymer as described above, typically via the functional group Y.

These and other objects and features of the invention will become more fully apparent when the following detailed description of the invention is read in conjunction with the accompanying drawings.

DETAILED DESCRIPTION OF THE INVENTION

I. Definitions

In describing and claiming the present invention, the following terminology will be used in accordance with the definitions described below.

As used in this specification, the singular forms "a," "an," and "the" include plural referents unless the context clearly dictates otherwise. Thus, for example, reference to a "polymer" includes a single polymer as well as two or more of the same or different polymers, reference to a "conjugate" refers to a single conjugate as well as two or more of the same or different conjugates, reference to an "excipient" includes a single excipient as well as two or more of the same or different excipients, and the like.

"Water soluble" indicates that a polymer or polymer segment is at least 35% (by weight) soluble, and preferably greater than 95% soluble, in water at room temperature. Typically, an unfiltered aqueous preparation of a "water soluble" polymer or segment transmits at least 75%, more preferably at least 95%, of the amount of light transmitted by the same solution after filtering. On a weight basis, a "water soluble" polymer or segment is preferably at least 35% (by weight) soluble in water, more preferably at least 50% (by weight) soluble in water, still more preferably at least 70% (by weight) soluble in water, and still more preferably at least 85% (by weight) soluble in water. It is most preferred, however, that the water-soluble polymer or segment is at least 95% (by weight) soluble in water or completely soluble in water.

As used herein, a "segment" can consist of a single monomeric unit, e.g. —($CH_2CH_2O$)—. Typically, however, a "polymer segment" contains multiple monomeric units. The "polymer segment" may be oligomeric; that is, including two to about ten monomeric units.

A "segmented polymer" refers to a polymer comprising at least two polymer segments joined by one or more linkages as defined herein, the linkage(s) being distinct from the monomeric units of the polymer segments.

A "monomeric unit" refers to one of the basic structural units of a polymer segment. In the case of homopolymeric segments, this can be defined as a structural repeating unit of the polymer segment. In the case of copolymers, a monomeric unit is more usefully defined as the residue of a monomer which was polymerized to form the polymer segment, since the structural repeating unit can include more than one monomeric unit.

"PEG" or "polyethylene glycol," as used herein, is meant to encompass any water-soluble poly(ethylene oxide). A "PEG polymer" can refer to a polymer having monomeric subunits of which greater than 50% are ethylene oxide (—CH$_2$CH$_2$O—) subunits; preferably, it refers to a polymer having monomeric subunits of which greater than 75%, greater than 90%, or greater than 95%, are ethylene oxide subunits. In one embodiment, substantially all, or all, monomeric subunits are ethylene oxide subunits, though the polymer may contain distinct end capping moieties, or functional groups, e.g. for conjugation. Typically, PEGs for use in the present invention will comprise one of the two following structures: "—(CH$_2$CH$_2$O)$_n$—" or "—(CH$_2$CH$_2$O)$_{n-1}$CH$_2$CH$_2$—," depending upon whether or not the terminal oxygen(s) has been displaced, e.g., during a synthetic transformation. The variable (n) is 3 to 3000, and the terminal groups and architecture of the overall PEG may vary. When PEG further comprises a linker moiety (to be described in greater detail below), the atoms comprising the linker (X'), when covalently attached to a PEG segment, do not result in formation of (i) an oxygen-oxygen bond (O—O, a peroxide linkage); or (ii) a nitrogen-oxygen bond (N—O, O—N).

A PEG polymer having non-(ethylene oxide) monomeric units is more preferably referred to as a PEG copolymer. Random or block copolymers of ethylene oxide and propylene oxide are a common example.

End-capped PEGs are commonly employed. The end capping group is generally a carbon-containing group attached to a terminal oxygen, typically comprised of 1-20 carbons and preferably alkyl or aralkyl (e.g., methyl, ethyl or benzyl), although saturated and unsaturated forms of these groups, as well as aryl, heteroaryl, cycloalkyl, heterocycle, and substituted forms of any of the foregoing are also envisioned. The end capping group may alternatively be a phospholipid. A preferred phospholipid is a dialkyl phosphatidyl ethanolamine, such as distearoyl phosphatidylethanolamine (DSPE), where the terminal amine of the phosphate head group can be used to link the lipid to the PEG chain via, for example, a carbamate linkage. Other suitable phospholipids include, for example, phosphatidyl cholines and phosphatidyl inositols. The end-capping group can also comprise a detectable label. Such labels include, without limitation, fluorescers, chemiluminescers, moieties used in enzyme labeling, colorimetric labels (e.g., dyes), metal ions, and radioactive moieties. The other (uncapped) terminus is a typically hydroxyl or another functional group, e.g. amine, that can be subjected to further chemical modification.

The architecture of a PEG molecule may vary. Specific PEG forms for use in the invention include PEGs having a variety of structures or geometries (e.g., branched, linear, forked, multiarmed, dendrimeric, and the like), to be described in greater detail below.

"Branched", in reference to the geometry or overall structure of a polymer, refers to a polymer having 2 or more polymer "arms". A branched polymer may possess 2 polymer arms, 3 polymer arms, 4 polymer arms, 6 polymer arms, 8 polymer arms or more. One particular type of highly branched polymer is a dendritic polymer or dendrimer, which, for the purposes of the invention, is considered to possess a structure distinct from that of a branched polymer.

A "branch point" refers to a bifurcation point comprising one or more atoms at which a polymer or linking group splits or branches from a linear structure into one or more additional polymer arms.

A "dendrimer" is a globular, size monodisperse polymer in which all bonds emerge radially from a central focal point or core with a regular branching pattern and with repeat units that each contribute a branch point. Dendrimers exhibit certain dendritic state properties such as core encapsulation, distinguishing them from other types of polymers.

"Substantially" or "essentially" means nearly totally or nearly completely, for instance, 95% or greater of some given quantity.

"Non-naturally occurring", with respect to a polymer of the invention, refers to a polymer that is not found in nature in its entirety, although it may contain one or more subunits or segments of subunits that are naturally occurring.

"Molecular mass" or "molecular weight" refers to the nominal average molecular mass of a polymer, typically determined by size exclusion chromatography, light scattering techniques, or intrinsic velocity determination in 1,2,4-trichlorobenzene. The polymer segments of the invention are typically polydisperse, possessing low polydispersity values of less than about 1.20.

The "linkage" or "linking group" between polymer segments, represented by X, refers to a linkage that is distinct from the monomeric units of the polymer segments. That is, there is a clear delineation between the structure of the linkage and the structure of the adjacent portions of the polymer segments. Typically, the linkage is a group formed by reaction between reactive functional groups on the precursor polymer segments; e.g. a nucleophilic functional group on the first polymer segment and an electrophilic group on the second polymer segment.

A "functional group" is a group that may be used, under normal conditions of organic synthesis, to form a covalent linkage between the structure to which it is attached and another structure, which typically bears a further functional group. The functional group generally includes multiple bond(s) and/or heteroatom(s). Preferred functional groups for use in the polymers of the invention are described below.

The term "reactive" refers to a functional group that reacts readily or at a practical rate under conventional conditions of organic synthesis. This is in contrast to those groups that either do not react or require strong catalysts or impractical reaction conditions in order to react (i.e., a "nonreactive" or "inert" group).

"Not readily reactive", with reference to a functional group present on a molecule in a reaction mixture, indicates that the group remains largely intact under conditions effective to produce a desired reaction in the reaction mixture.

An "activated derivative" of a carboxylic acid refers to a carboxylic acid derivative which reacts readily with nucleophiles, generally much more readily than the underivatized carboxylic acid. Activated carboxylic acids include, for example, acid halides (such as acid chlorides), anhydrides, carbonates, and esters. Such esters include, for example, imidazolyl esters, and benzotriazole esters, and imide esters, such as N-hydroxysuccinimidyl (NHS) esters. An activated derivative may be formed in situ by reaction of a carboxylic acid with one of various reagents, e.g. benzotriazol-1-yloxy tripyrrolidinophosphonium hexafluorophosphate (PyBOP), preferably used in combination with 1-hydroxy benzotriazole (HOBT) or 1-hydroxy-7-azabenzotriazole (HOAT); O-(7-azabenzotriazol-1-yl)-N,N,N',N"-tetramethyluronium hexafluorophosphate (HATU); or bis(2-oxo-3-oxazolidinyl) phosphinic chloride (BOP-Cl).

A "protecting group" is a moiety that prevents or blocks reaction of a particular chemically reactive functional group in a molecule under certain reaction conditions. The protecting group will vary depending upon the type of chemically reactive group being protected as well as the reaction conditions to be employed and the presence of additional reactive or protecting groups in the molecule. Functional groups which may be protected include, by way of example, carboxylic acid groups, amino groups, hydroxyl groups, thiol groups, carbonyl groups and the like. Representative protecting groups for carboxylic acids include esters (such as a p-methoxybenzyl ester), amides and hydrazides; for amino groups, carbamates (such as tert-butoxycarbonyl) and amides; for hydroxyl groups, ethers and esters; for thiol groups, thioethers and thioesters; for carbonyl groups, acetals and ketals; and the like. Such protecting groups are well-known to those skilled in the art and are described, for example, in T. W. Greene and G. M. Wuts, *Protecting Groups in Organic Synthesis*, Third Edition, Wiley, New York, 1999, and references cited therein.

A functional group in "protected form" refers to a functional group bearing a protecting group. As used herein, the term "functional group" or any synonym thereof is meant to encompass protected forms thereof.

The term "spacer" or "spacer moiety" refers to an atom or, more typically, a collection of atoms, used to link interconnecting moieties, such as the terminus of a polymer segment and a functional group or linking group. The spacer moieties of the invention may, be hydrolytically stable, including bonds such as alkyl, ether, or amide. Particularly preferred are alkyl or alkyl ether spacer groups. Alternatively, they may include a physiologically hydrolyzable or enzymatically degradable linkage, such as an ester or disulfide.

"Alkyl" refers to a saturated hydrocarbon chain, typically ranging from about 1 to 20 carbon atoms in length, more typically about 1 to 12 carbon atoms in length. Such hydrocarbon chains may be branched or, more typically, linear. Exemplary alkyl groups include ethyl, propyl, butyl, pentyl, 1-methylbutyl, 1-ethylpropyl, 3-methylpentyl, and the like. As used herein, "alkyl" includes cycloalkyl having three or more carbon atoms.

"Lower alkyl" refers to an alkyl group containing from 1 to 6 carbon atoms, preferably 1 to 4 carbon atoms, and may be linear or branched, as exemplified by methyl, ethyl, isopropyl, isobutyl, n-butyl, and t-butyl.

"Cycloalkyl" refers to a saturated or unsaturated cyclic hydrocarbon radical, including bridged, fused, or spiro cyclic compounds, preferably having 3 to about 12 carbon atoms, more preferably 3 to about 8.

"Non-interfering substituents" are groups that are typically non-reactive with other functional groups contained within the same molecule, under normal conditions of organic synthesis.

The term "substituted", as in, for example, "substituted alkyl," refers to a moiety (e.g., an alkyl group) substituted with one or more non-interfering substituents, such as, but not limited to, $C_3$-$C_8$ cycloalkyl; halo, e.g., fluoro, chloro, bromo, or iodo; cyano; nitro; alkoxy; hydroxy; amino; alkylamino; carboxylic acid or ester; sulfonic acid or ester; phenyl; substituted phenyl; and the like. "Substituted aryl" refers to aryl having one or more non-interfering substituents in any orientation (i.e., ortho, meta, or para).

"Alkoxy" refers to an —OR group, wherein R is alkyl or substituted alkyl, preferably $C_1$-$C_{20}$ alkyl (e.g., methoxy, ethoxy, propyloxy, benzyl, etc.), more preferably $C_1$-$C_7$.

As used herein, "alkenyl" refers to a branched or unbranched hydrocarbon having 2 to about 15 carbon atoms and containing at least one double bond, such as ethenyl, n-propenyl, isopropenyl, n-butenyl, isobutenyl, octenyl, decenyl, tetradecenyl, and the like.

The term "alkynyl" as used herein refers to a branched or unbranched hydrocarbon having 2 to about 15 carbon atoms and containing at least one triple bond, such as ethynyl, n-propynyl, isopropynyl, n-butynyl, isobutynyl, octynyl, or decynyl.

The term "aryl" refers to a monovalent aromatic hydrocarbon having a single ring (i.e., phenyl) or fused rings (i.e., naphthalene). Unless otherwise defined, such aryl groups typically contain from 4 to 10 carbon ring atoms. Multiple aryl rings may be fused, as in naphthyl, or unfused (linked), as in biphenyl. Aryl rings may also be fused or linked with one or more cyclic hydrocarbon, heteroaryl, or heterocyclic rings. Representative aryl groups include, by way of example, phenyl, naphthalene-1-yl, naphthalene-2-yl, and the like.

"Aralkyl" refers to an alkyl, preferably lower ($C_1$-$C_4$, more preferably $C_1$-$C_2$) alkyl, substituent which is further substituted with an aryl group; examples are benzyl and phenethyl.

As used herein, "aryl" includes heteroaryl. The term "heteroaryl" refers to a monovalent aromatic group containing in the ring at least one heteroatom (typically 1 to 3 heteroatoms) selected from nitrogen, oxygen or sulfur. Heteroaryl rings may also be fused with one or more cyclic hydrocarbon, heterocyclic, aryl, or heteroaryl rings. Unless otherwise defined, such heteroaryl groups typically contain from 5 to 10 total ring atoms. Representative heteroaryl groups include, by way of example, monovalent species of pyrrole, imidazole, thiazole, oxazole, furan, thiophene, triazole, pyrazole, isoxazole, isothiazole, pyridine, pyrazine, pyridazine, pyrimidine, triazine, indole, benzofuran, benzothiophene, benzimidazole, benzthiazole, quinoline, isoquinoline, quinazoline, quinoxaline and the like.

"Heterocycle" or "heterocyclic" means one or more rings of 5-12 atoms, preferably 5-7 atoms, with or without unsaturation or aromatic character and having at least one ring atom which is not a carbon. Preferred heteroatoms include sulfur, oxygen, and nitrogen.

"Substituted heteroaryl" refers to heteroaryl having one or more non-interfering groups as substituents.

A "heterocycle" refers to a non-aromatic ring, preferably a 5- to 7-membered ring, whose ring atoms are selected from the group consisting of carbon, nitrogen, oxygen and sulfur. Preferably, the ring atoms include 3 to 6 carbon atoms. Such heterocycles include, for example, pyrrolidine, piperidine, piperazine, and morpholine.

A "substituted heterocycle" is a heterocycle having one or more side chains formed from non-interfering substituents.

An "electrophile" refers to an atom or collection of atoms, which may be ionic, having an electrophilic center, i.e., a center that is electron seeking, capable of reacting with a nucleophile.

A "nucleophile" refers to an atom or collection of atoms, which may be ionic, having a nucleophilic center, i.e., a center that seeks an electrophilic center, capable of reacting with an electrophile.

A "physiologically hydrolyzable" bond is a bond that reacts with water (i.e., is hydrolyzed) under physiological conditions. Such a bond is therefore degradable in water or aqueous media, e.g. blood, under physiological conditions. Such bonds generally include, for example, carboxylate esters, phosphate esters, anhydrides, acetals, ketals, acyloxyalkyl ether, imines, orthoesters, and oligonucleotide bonds.

An "enzymatically degradable linkage" is a linkage that is subject to degradation by one or more enzymes. Such bonds generally include, for example, carboxylate esters, phosphate esters (e.g. oligonucleotide linkages), and peptide bonds.

A "hydrolytically stable" linkage or bond refers to a chemical bond, typically a covalent bond, that is substantially stable in water; i.e. it does not undergo hydrolysis under physiological conditions to any appreciable extent over an extended period of time. Examples of hydrolytically stable linkages include, for example, carbon-carbon bonds (e.g., in aliphatic chains), ethers, amines, and, to a lesser extent, amides. Generally, a hydrolytically stable linkage is one that exhibits a rate of hydrolysis of less than about 1-2% per day under physiological conditions. Hydrolysis rates of representative chemical bonds can be found in most standard chemistry textbooks.

"Multifunctional", in the context of a polymer of the invention, refers to a polymer having 2 or more, preferably 3 or more, functional groups, which may be the same or different. Multifunctional polymers of the invention will typically contain from about 3-100 functional groups, or from 3-50 functional groups, or from 3-25 functional groups, or from 3-15 functional groups, or from 3 to 10 functional groups, or will contain 3, 4, 5, 6, 7, 8, 9 or 10 functional groups within the polymer backbone. A "bifunctional" polymer is a polymer having two functional groups, either the same (i.e., homobifunctional) or different (i.e., heterobifunctional).

Reference to a compound which is basic or acidic is typically intended to encompass neutral, charged, and any corresponding salt forms thereof. It will be apparent to those skilled in the art when a particular form is most suitable for a desired purpose, such as a desired reaction or for purposes or solubility.

A "hydrogel" is a material that absorbs a solvent (e.g. water), undergoes rapid swelling without discernible dissolution, and maintains three-dimensional networks capable of reversible deformation. Hydrogels may be uncrosslinked or crosslinked. Covalently (chemically) crosslinked networks of hydrophilic polymers, such as PEG, can form hydrogels (or aquagels) in the hydrated state. Uncrosslinked hydrogels are typically block copolymers having hydrophilic and hydrophobic regions. These uncrosslinked materials can form hydrogels when placed in an aqueous environment, due to physical crosslinking forces resulting from ionic attractions, hydrogen bonding, Van der Waals forces, etc. They are able to absorb water but do not dissolve due to the presence of hydrophobic and hydrophilic regions.

A "polymer conjugate" as used herein refers to a water soluble segmented polymer covalently attached to a further moiety, such as a pharmacologically active molecule or surface.

A "pharmacologically active" agent includes any drug, compound, composition of matter or mixture desired to be delivered to a subject, e.g. therapeutic agents, diagnostic agents, or drug delivery agents, including targeting agents, which provides or is expected to provide some pharmacologic, often beneficial, effect that can be demonstrated in vivo or in vitro. Such agents may include biomolecules, e.g. peptides, proteins, carbohydrates, nucleic acids, nucleosides, oligonucleotides, and lipids, or analogs thereof, as well as dyes, liposomes, microparticles, and therapeutic "small molecule" compounds. Examples of lipids include phospholipids, glycolipids, such as cerebrosides and gangliosides, sphingolipids, fatty diacylglycerides, triglycerides, glycosylglycerides, and steroids, including sterols.

A "small molecule" compound may be defined broadly as an organic, inorganic, or organometallic compound which is not a biomolecule as described above. Typically, such compounds have molecular weights of less than about 1000.

Classes of therapeutic agents that are suitable for use with the invention include, but are not limited to, antibiotics, fungicides, anti-viral agents, anti-inflammatory agents, anti-tumor agents, cardiovascular agents, anti-anxiety agents, hormones, growth factors, steroidal agents, and the like.

A "pharmaceutically acceptable excipient" or "pharmaceutically acceptable carrier" refers to an excipient that can be included in the compositions of the invention and that causes no significant adverse toxicological effects to the subject or patient to which the composition is administered. "Pharmacologically effective amount," "physiologically effective amount," and "therapeutically effective amount" are used interchangeably herein to mean the amount of a PEG-active agent conjugate present in a pharmaceutical preparation that is needed to provide a desired level of active agent and/or conjugate in the bloodstream or in the target tissue. The precise amount will depend upon numerous factors, e.g., the particular active agent, the components and physical characteristics of pharmaceutical preparation, intended patient population, patient considerations, and the like, and can readily be determined by one skilled in the art, based upon the information provided herein and available in the relevant literature.

The term "patient" refers to a living organism suffering from or prone to a condition that can be prevented or treated by administration of a polymer-agent conjugate as described herein, and includes both humans and animals.

II. Segmented Polymers of the Invention

The invention includes medium to high molecular weight, functionalized, water soluble segmented polymers and methods for preparing them. The polymers of the invention include a "medium to high" molecular weight segment, which may be designated $POLY_A$, which imparts desired physical and pharmacological properties to a conjugate of the polymer with a pharmacological agent. This segment is covalently linked to a "low molecular weight" segment, which may be designated $POLY_B$, typically having a composition similar to $POLY_A$. In preparing the conjugate, as described further below, synthetic transformations such as attachment of functional groups, linker moieties, and/or spacer groups and purification steps are advantageously carried out on the $POLY_B$ segment, which is then linked, at a later stage in the preparation, to $POLY_A$.

Large polymeric impurities are more difficult to separate from the desired product than are smaller ones, and the products of these reactions involving these polymers typically include unreacted reagents, bifunctional components that can result in cross linking, partially reacted components, and other polymeric impurities. The synthetic strategy described herein reduces the number of synthetic transformations carried out on $POLY_A$ and thus reduces the need for laborious purification of higher molecular weight intermediates.

A. Size and Molecular Weight Ranges

The molecular weight of the $POLY_B$ segment is generally low, e.g. preferably below 5000, and more preferably below 2000, for purposes of synthesis and purification, as discussed above. The molecular weight of the $POLY_A$ segment, and the overall polymer, are selected in accordance with the intended use of the polymer conjugate.

For example, it is well established that higher molecular weight polymer conjugates generally provide longer circulation times, as well as significant tumor accumulation (e.g., Y. Murakami et al., *Drug. Del.* 4:23-32, 1997), when used for drug delivery applications. However, in some cases, such as administration of thrombolytic drugs, or many diagnostic applications, long circulation times may be less desirable. In addition, the use of a lower molecular weight polymer (such as the "medium" molecular weight ranges for PEG described herein) can provide greater drug loading for a smaller mass of conjugate administered. Larger polymers may also be more likely to block reactive sites of attached drugs (although this can frequently be addressed via the use of cleavable conjugates). In view of these factors, the preferred molecular weight of $POLY_A$ can vary widely.

Preferably, the number of monomeric units in $POLY_A$ is between 4 and about 2000, and the number of monomeric units in $POLY_B$ is between 1 and about 120, as long as $POLY_B$ has a lower molecular weight than that of $POLY_A$. Typically, $POLY_B$ will have fewer monomeric units, as well as a lower molecular weight, than POLY$_A$. Preferably, the molecular weight of POLY$_B$ is at most half that of POLY$_A$ (excluding functional groups).

It can be seen that oligomeric and even monomeric lengths of POLY$_B$ are included. In selected embodiments, POLY$_B$ has at least two, or at least three, monomeric units. POLY$_B$ may have exactly two or exactly three monomeric units. In further embodiments, the segment POLY$_B$ has from two to about 15 monomeric units. Preferably, when POLY$_B$ consists of one or two monomeric PEG units, in a segmented PEG polymer where POLY$_A$ is mPEG, the functional group Y is not a maleimide group.

The molecular weight of the POLY$_B$ segment is typically in the range of from about 100 Da to about 10,000 Da, and more typically from about 100 Da to about 5000 Da, depending on the molecular weight of the individual monomeric units. In selected embodiments, POLY$_B$ has 2, 3, 4, 5, 10, 15, 25, 35, 45, 75 or 100 monomeric units. These ranges correspond, for example, to poly(ethylene glycol) segments having molecular weights of about 88, 132, 176, 220, 440, 660, 1100, 1540, 1980, 3300, and 4400 Daltons, respectively. In other selected embodiments, a PEG POLY$_B$ segment has a molecular weight of about 100, 500, 1000, 1500, 2000, 3000, or 5000. Selected ranges of molecular weight include from 44 to about 4400, 44 to about 1500, 220 to about 2000, and about 2000 to about 3300. Numerous low molecular weight PEGs, having molecular weights of, for example, 200, 300, 400, 600, 900, 1000, 2000, 3200, 3400, and 5000, are commonly available commercially.

POLY$_A$ may be a "high" molecular weight segment, i.e. having more than 200 monomeric repeating units, or a "medium" molecular weight segment, i.e. having 4 to about 200 monomeric repeating units. In selected embodiments, POLY$_A$ is a "medium molecular weight" segment having at least 10, 20, 25, 50, 100, 125, 150, or 175 monomeric units, but at most 200 monomeric units. These values correspond, for example, to poly(ethylene glycol) segments having molecular weights of at least about 440, 880, 1100, 2200, 4400, 5500, 6600, and 7700 Daltons, respectively, up to about 8800 Daltons. Typical ranges include about 25, about 50, about 100, or about 150-200 monomeric units.

In other selected embodiments, a "high molecular weight" POLY$_A$ segment has at least 200, 250, 500, 1000, 1500, or 2000 or more monomeric units. These ranges correspond, for example, to poly(ethylene glycol) segments having molecular weights of at least about 8800, 11,000, 22,000, 44,000, 66,000, or 88,000 or more Daltons, respectively.

In selected embodiments of segmented PEG-based polymers, where each of POLY$_A$ and POLY$_B$ is a poly(ethylene glycol) segment, POLY$_A$ has a medium molecular weight range selected from about 200-5000, about 500-2000, and about 1000-1500. In other embodiments of PEG-based segmented polymers, POLY$_A$ has a high molecular weight range selected from about 8800 to about 20000, about 15000 to about 50000, and about 20000 to about 90000. Commercially available PEGs include those having a nominal molecular weight of 10,000, 12,000, 15,000, 18,000, and 20,000, 30,000, 40,000 and above. Branched PEGs are readily available at higher molecular weights.

B. Composition

Various monomers are available for preparing the water soluble segmented polymers of the invention. The segments of the polymer (i.e. POLY$_A$ and POLY$_B$) can be formed from a single monomer (homopolymeric) or two or three monomers (copolymeric). Preferably, each such segment is a copolymer of two monomers or, more preferably, a homopolymer. The monomer(s) employed result in a segmented polymer that is water soluble as defined herein; that is, >95% water soluble, preferably >99% water soluble, in water at room temperature at physiological pH (about 7.2-7.6).

Accordingly, each of the segments designated POLY$_A$ and POLY$_B$ independently comprises up to three different monomers selected from the group consisting of: alkylene glycol, such as ethylene glycol or propylene glycol; olefinic alcohol, such as vinyl alcohol, 1-propenol or 2-propenol; vinyl pyrrolidone; hydroxyalkyl methacrylamide or hydroxyalkyl methacrylate, where alkyl is preferably methyl; saccharide; α-hydroxy acid, such as lactic acid or glycolic acid; phosphazene, oxazoline, and N-acryloylmorpholine. Preferred monomer types include alkylene glycol, olefinic alcohol, hydroxyalkyl methacrylamide or methacrylate, N-acryloylmorpholine, and α-hydroxy acid. Preferably, each segment is, independently, a copolymer of two monomers selected from this group, or, more preferably, a homopolymer of one monomer selected from this group. Typically, POLY$_A$ and POLY$_B$ will include the same monomer(s).

The two monomers in a copolymer may be of the same monomer type, for example, two alkylene glycols, such as ethylene glycol and propylene glycol. In selected embodiments, each of POLY$_A$ and POLY$_B$ is independently a poly(alkylene glycol). For example, each of POLY$_A$ and POLY$_B$ may be selected from poly(ethylene glycol) and an ethylene glycol/propylene glycol copolymer.

The monomers in a copolymer may also be of different monomer types. For example, the segmented water soluble polymer can be prepared with one or more weak or degradable linkages in the polymer backbone, such as a poly(alkylene glycol) having periodic ester linkages in the polymer backbone.

In preferred embodiments, each of POLY$_A$ and POLY$_B$ is a poly(ethylene glycol). PEG polymers are typically clear, colorless, odorless, soluble in water, stable to heat, inert to many chemical agents, and non-toxic, and do not hydrolyze or deteriorate (unless specifically designed to do so). Poly(ethylene glycol) is highly biocompatible and substantially non-immunogenic. When conjugated to a pharmacologically active agent, the PEG molecule tends to mask the agent and can reduce or eliminate any immune response to the agent. PEG conjugates tend not to produce a substantial immune response or cause clotting or other undesirable effects.

The unconjugated terminus of the water soluble polymer, typically a terminus of POLY$_A$, is generally capped to render it unreactive. The capping group may be, for example, $C_1$-$C_{20}$ alkoxy or aryloxy, more preferably $C_1$-$C_{10}$ alkoxy or aryloxy. In further selected embodiments, R is $C_1$-$C_5$ alkoxy or benzyloxy. A common is example is a methoxy-terminated PEG, designated mPEG.

The capping group may also be a phospholipid. A preferred phospholipid is a dialkyl phosphatidylethanolamine, such as distearoyl phosphatidylethanolamine (DSPE; see structure below). Other suitable phospholipids include, for example, phosphatidyl serines, phosphatidyl glycerols, phosphatidyl inositols, and phosphatidyl cholines, all of which are well known in the art and available commercially. A reactive group on the phosphate head group can be used to link the lipid to a PEG chain; for example, the terminal amine in DSPE can be linked to PEG via a carbamate linkage.

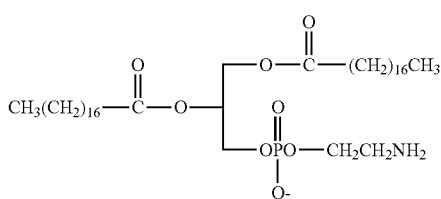

C. Linkages

The linkage X between the polymer segments is typically formed by reaction of a functional group on a terminus of $POLY_A$ with a corresponding functional group on a terminus of $POLY_B$. For example, an amino group on $POLY_A$ may be reacted with an activated carboxylic acid derivative on $POLY_B$, or vice versa, to produce an amide linkage. Alternatively, reaction of an amine with an activated carbonate (e.g. succinimidyl or benzotriazyl carbonate) forms a carbamate linkage, and reaction of an amine with an isocyanate (R—N=C=O) forms a urea linkage (R—NH—(C=O)—NH—R'). In selected embodiments, X comprises an amide, a carbamate, a carbonate, an ester, a urea, an amine, a thioether, or a disulfide. These linkages and methods of forming them are well known in the art. Functional groups such as those discussed in Section D below, and illustrated in the working examples, are typically used for forming the linkages. The linkage may also comprise (or be adjacent to or flanked by) spacer groups, as described further below.

Typically, the terminus of $POLY_A$ not bearing a functional group is capped to render it unreactive. As described above, suitable capping groups include alkoxy groups, aryloxy groups, and phospholipids, such as DSPE. When $POLY_B$ includes a further functional group (Y) for formation of a conjugate, the group Y is either selected such that it is unreactive under the conditions of formation of the linkage X, or it is protected during the formation of the linkage X.

In the segmented polymer compositions of the invention, the linkage X is distinct from the monomeric units of the polymer segments and the linkages between the monomers, such that there is a clear delineation between the structure of the linkage and the structure of the polymer segments. For example, in a segmented polymer in which $POLY_A$ and/or $POLY_B$ is a PEG copolymer having periodic carboxylic ester linkages for the purpose of biodegradability, the linkage X between $POLY_A$ and $POLY_B$ would not be such a carboxylic ester linkage (and clearly would not be a —CH$_2$—CH$_2$O— linkage).

D. Functional Groups for Conjugation

The segmented polymers include a functional group, Y, attached to $POLY_A$ and/or $POLY_B$, typically on $POLY_B$, which is useful for forming a conjugate of the polymer, e.g., with a pharmacologically active agent, surface, solid support, or the like, as described in greater detail below. The functional group typically comprises an electrophilic or nucleophilic group that provides for covalent attachment of a desired agent to the segmented polymer. Examples of nucleophilic groups include hydroxyl, amine, hydrazine (—NHNH$_2$), hydrazide (—C(O)NHNH$_2$), and thiol. Preferred nucleophiles include amine, hydrazine, hydrazide, and thiol, particularly amine.

Examples of electrophilic functional groups include carboxylic acid, carboxylic ester, particularly imide esters, orthoester, carbonate, isocyanate, isothiocyanate, aldehyde, ketone, thione, alkenyl, acrylate, methacrylate, acrylamide, sulfone, maleimide, disulfide, iodo, epoxy, sulfonate, thiosulfonate, silane, alkoxysilane, halosilane, and phosphoramidate. More specific examples of these groups include succinimidyl ester or carbonate, imidazoyl ester or carbonate, benzotriazole ester or carbonate, vinyl sulfone, chloroethylsulfone, vinylpyridine, pyridyl disulfide, iodoacetamide, glyoxal, dione, mesylate, tosylate, and tresylate (2,2,2-trifluoroethanesulfonate).

Also included are sulfur analogs of several of these groups, such as thione, thione hydrate, thioketal, etc., as well as hydrates or protected derivatives of any of the above moieties (e.g. aldehyde hydrate, hemiacetal, acetal, ketone hydrate, hemiketal, ketal, thioketal, thioacetal). Another useful conjugation reagent is 2-thiazolidine thione.

As noted above, an "activated derivative" of a carboxylic acid refers to a carboxylic acid derivative which reacts readily with nucleophiles, generally much more readily than the underivatized carboxylic acid. Activated carboxylic acids include, for example, acid halides (such as acid chlorides), anhydrides, carbonates, and esters. Such esters include imide esters, of the general form —(CO)O—N[(CO)—]$_2$; for example, N-hydroxysuccinimidyl (NHS) esters or N-hydroxyphthalimidyl esters. Also preferred are imidazolyl esters and benzotriazole esters. Particularly preferred are activated propionic acid or butanoic acid esters, as described in co-owned U.S. Pat. No. 5,672,662. These include groups of the form —(CH$_2$)$_{2-3}$C(=O)O-Q, where Q is preferably selected from N-succinimide, N-sulfosuccinimide, N-phthalimide, N-glutarimide, N-tetrahydrophthalimide, N-norbornene-2,3-dicarboximide, benzotriazole, 7-azabenzotriazole, and imidazole.

Other preferred electrophilic groups include succinimidyl carbonate, maleimide, benzotriazole carbonate, glycidyl ether, imidazoyl carbonate, p-nitrophenyl carbonate, acrylate, tresylate, aldehyde, and orthopyridyl disulfide.

These electrophilic groups are subject to reaction with nucleophiles, e.g. hydroxy, thio, or amino groups, to produce various bond types. For example, carboxylic acids and activated derivatives thereof, which include orthoesters, succinimidyl esters, imidazolyl esters, and benzotriazole esters, react with the above types of nucleophiles to form esters, thioesters, and amides, respectively, of which amides are the most hydrolytically stable. Carbonates, including succinimidyl, imidazolyl, and benzotriazole carbonates, will react with hydroxyl or amino groups to form further carbonates or carbamates, respectively. Isocyanates (R—N=C=O) react with hydroxyl or amino groups to form, respectively, carbamate (RNH—C(O)—OR') or urea (RNH—C(O)—NHR') linkages. Phosphoramidites can be reacted with hydroxyl reagents, followed by oxidation, to form phosphate esters (as in conventional oligonucleotide synthesis).

Aldehydes, ketones, glyoxals, diones and their hydrates or alcohol adducts (i.e. aldehyde hydrate, hemiacetal, acetal, ketone hydrate, hemiketal, and ketal) are preferably reacted with amines, followed by reduction of the resulting imine, if desired, to give an amine linkage (reductive amination). Alternatively, these groups can be reacted with hydroxyl containing groups, to form further acetals, ketals, etc. In these cases, the linkages formed are subject to hydrolytic degradation, which may be desirable, as discussed further below.

Several of the electrophilic functional groups include electrophilic double bonds to which nucleophilic groups, such a thiols, can be added, to form, for example, thioether bonds. These groups include maleimides, vinyl sulfones, vinyl pyridine, acrylates, methacrylates, and acrylamides. Other groups comprise leaving groups which can be displaced by a nucleophile; these include chloroethyl sulfone, pyridyl disulfides (which include a cleavable S—S bond), iodoacetamide, mesylate, tosylate, thiosulfonate, and tresylate. Epoxides react by ring opening by a nucleophile, to form, for example, an ether or amine bond. Silanes, including halosilanes and alkoxysilanes, react with hydroxy- or oxide-containing compounds, or surfaces such as glass, to form siloxanes.

The use of several of these groups is described in the following representative references: N-succinimidyl carbonate (U.S. Pat. Nos. 5,281,698 and 5,468,478), N-succinimidyl succinate (Abuchowski et al., *Cancer Biochem. Biophys.* 7:175, 1984), N-succinimidyl ester (U.S. Pat. No. 4,670,417), N-succinimidyl propionate (U.S. Pat. No. 5,672,662), N-succinimidyl butanoate (U.S. Pat. No. 5,672,662), benzotriazole carbonate (U.S. Pat. No. 5,650,234), propionaldehyde (U.S. Pat. No. 5,824,784) and acetaldehyde, which are typically protected as the diethyl acetal (U.S. Pat. No. 5,990,237), glycidyl ether (Elling et al., *Biotech. Appl. Biochem.* 13:354, 1991), imidazolyl ester (Tondelli et al., *J. Controlled Release* 1:251, 1985), p-nitrophenyl carbonate (Sartore et al., *Appl. Biochem. Biotech.* 27:45, 1991), maleimide (Kogan, *Synthetic Comm.* 22:2417, 1992), orthopyridyl disulfide (Woghiren et al., *Bioconj. Chem.* 4:314, 1993), acrylate (Sawhney et al., *Macromolecules* 26:581, 1993), vinyl sulfone (U.S. Pat. No. 5,900,461), and 2-thiazolidine thione (Greenwald et al., U.S. Pat. No. 5,349,001).

E. Spacers

One or more spacer groups may be employed to link the functional group Y, or the linkage X, to a terminus or branch point of segment $POLY_A$ or $POLY_B$. Preferably, the atoms making up the spacer moiety comprise some combination of carbon, oxygen, hydrogen, nitrogen, and, less frequently, sulfur atoms. The spacer generally does not include bonds that are reactive under physiological conditions, unless it is desired that the spacer be hydrolytically or enzymatically cleavable. Accordingly, the spacer(s) may be hydrolytically stable, including, for example, bonds such as alkyl, ether, keto, amide, urea, or sulfide, or they may include a physiologically hydrolyzable or enzymatically degradable linkage, such as an ester, carbonate, carbamate, or disulfide.

Preferred spacer groups include hydrocarbon spacers, e.g. linear or branched divalent alkyl chains having 4 to about 24, preferably 4 to about 12, more preferably 4 to 8, carbon atoms, e.g. as tetramethylene, pentamethylene, or hexamethylene. Other hydrocarbon-based spacers include bivalent cycloalkyl groups, preferably $C_3$-$C_8$ cycloalkyl, such as cyclopropadiyl, cyclobutadiyl, cyclopentadiyl, cyclohexadiyl, and cycloheptadiyl. The cycloalkyl group can be substituted with one or more alkyl groups, preferably $C_1$-$C_6$ alkyl groups.

III. Structural Variants

The segmented polymer and/or the individual segments, $POLY_A$ and $POLY_B$, can have various architectural forms, e.g. linear, branched, forked, multi-armed, or dendrimeric. Some of these forms, such as forked or multiarmed, typically contain two or more functional groups for conjugation. Such multifunctional polymers can be used to conjugate multiple therapeutic molecules and/or targeting agents to a single carrier. They are also useful for linking macromolecules to surfaces, for use in assays or biosensors, for example. The water soluble segmented polymers can also be used to form crosslinked or uncrosslinked hydrogels, which are particularly useful for drag delivery devices and biocompatible wound coverings.

A. Linear Polymers

A linear polymer of the invention has the general structure:

$$POLY_A\text{-}X\text{-}POLY_B\text{-}Y \tag{Ia}$$

or

$$POLY_B\text{-}X\text{-}POLY_A\text{-}Y \tag{Ib}$$

where structure Ia is generally preferred. Linear concatamers, e.g. containing multiple linked $POLY_A$ and/or $POLY_B$ segments, may also be provided.

In further selected embodiments, a linear segmented PEG polymer is provided, having the structure:

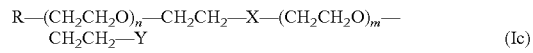
$$R\text{—}(CH_2CH_2O)_n\text{—}CH_2CH_2\text{—}X\text{—}(CH_2CH_2O)_m\text{—}CH_2CH_2\text{—}Y \tag{Ic}$$

where:
R is a functional group or, preferably, a capping group;
n is at least 4 and at most about 2000,
m is between 1 and about 120, where m<n,
X is a linking group, as described herein, and
Y is a functional group, as described herein, which may be the same or different from R when R is a functional group. In selected embodiments, n is at most about 1000, at most about 500, or at most about 200.

The capping group may be, for example, $C_1$-$C_{20}$ alkoxy or aryloxy, more preferably $C_1$-$C_{10}$ alkoxy or aryloxy. In further selected embodiments, R is $C_1$-$C_5$ alkoxy or benzyloxy.

The capping group may also be a phospholipid. A preferred phospholipid is a dialkyl phosphatidylethanolamine, such as distearoyl phosphatidylethanolamine (DSPE), where the terminal amine of the phosphate head group can be used to link the lipid to the PEG chain via, for example, a carbamate linkage. Other suitable phospholipids include, for example, phosphatidyl cholines and phosphatidyl inositols.

Several exemplary linear segmented PEGs are shown in Examples 4, 6-7, 9-14, 16-17 and 20 below. A particularly preferred class of compound is illustrated in Examples 14A-C. These compounds have the structure:

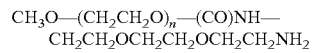
$$CH_3O\text{—}(CH_2CH_2O)_n\text{—}(CO)NH\text{—}CH_2CH_2OCH_2CH_2OCH_2CH_2NH_2$$

The molecular weight of the segmented polymer is dependent on the size of the $POLY_A$ segment $(CH_2CH_2O)_n$ and is preferably selected from about 1000, about 5000, about 10000, and about 20000.

B. Branched Polymers

A "branched" polymer of the invention, in one aspect, refers to any segmented polymer as described herein in which $POLY_A$ and/or $POLY_B$, preferably $POLY_A$, is branched. The polymer segment may include branch points within its monomeric units, e.g. where some percentage of monomers is trifunctional or greater. The polymer segment may also comprise multiple polymer arms connected to a common linking group.

Certain branched polymers of the invention can be represented schematically as follows:

$$(POLY_A\text{-}X\text{-}POLY_B)_p\text{-}L\text{-}Y \tag{IIa}$$

or

$$(POLY_A\text{-}X)_p\text{-}L\text{-}POLY_B\text{-}Y \tag{IIb}$$

or

$$(POLY_A)_p\text{-}L\text{-}X\text{-}POLY_B\text{-}Y \tag{IIc}$$

where $POLY_A$, $POLY_B$, X, and Y are as defined above; L represents a branched spacer group; and p is $\geq 2$, preferably 2 to about 100, more preferably 2 to about 10. In one embodiment, p is 2.

For example, in structure Ia above, multiple polymer arms, each comprising $POLY_A$ linked to $POLY_B$, are attached, via a branched spacer group, to a single functional group Y. Alternatively, $POLY_A$ can be a branched polymer segment, having 2 or more polymer arms, which is attached via a covalent linkage to a single POLY$_B$-Y segment, as in structure IIc or IIb above.

Preferably, the branch point in the branched spacer group L comprises a carbon atom (—CH<), though it may also comprise a nitrogen atom (—N<). The branch point is linked to adjacent moieties, such as X, Y or a polymer segment, directly or by chains of atoms of defined length. Each chain of atoms may comprise, for example, alkyl, ether, ester, or amide linkages, or combinations thereof.

Illustrative branched POLY$_A$ segments include those described in U.S. Pat. No. 5,932,462, the content of which is incorporated herein by reference. Generally speaking, branched POLY$_A$ segments of this sort are characterized by the structure:

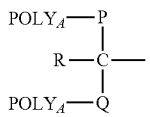

where POLY$_A$ is as defined herein, and P and Q are hydrolytically stable linkage fragments joining the polymer arms, POLY$_A$, to the central carbon atom, C. R is typically H or methyl, but may comprise a linkage fragment joined to an additional polymer arm, POLY$_A$.

In selected embodiments of structures IIa-c above, the POLY$_A$ segment is a PEG segment (PEG$_A$) comprising at least 4 and at most about 2000 —CH$_2$CH$_2$O— monomeric units; X is selected from an amide, a carbamate, a carbonate, an ester, a urea, an amine, a thioether, and a disulfide; and the POLY$_B$ segment is a PEG segment (PEG$_B$) comprising at least 1, preferably at least 2, and at most about 120 —CH$_2$CH$_2$O— monomeric units, with the proviso that PEG$_B$ has a lower molecular weight than that of PEG$_A$. Preferred ranges of p include 1-100, 2-20, and 2-10.

In these structures and in others described herein, PEG$_A$ represents an embodiment of POLY$_A$, and preferably has a size and molecular weight range as described for POLY$_A$ above. Examples of molecular weight ranges include about 10000-40000, or, for medium molecular weight embodiments, about 200-1000 or 1000-5000. PEG$_A$ preferably comprises an end-capping group, such as alkoxy or a phospholipid. In selected embodiments, X comprises a carbamate, an amide, a carbonate, an ester, a urea, an amine, a thioether, or a disulfide. and Y comprises an amine or protected amine. Preferably, X comprises a carbamate, an amide, a urea, or a carbonate.

One example of a branched PEG segment which could be represented by (POLY$_A$-X)$_2$-L- above is a PEG-disubstituted lysine having the structure:

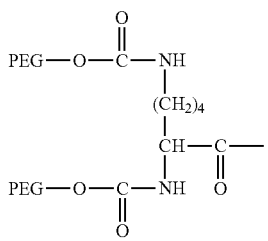

The preparation of an exemplary branched polymer of the invention, in accordance with the structure (POLY$_A$)$_p$-L-X-POLY$_B$-Y (IIc) presented above, is provided in Examples 18 and 19, where a branched POLY$_A$ segment (each branch comprising 20 kDa PEG) is linked to a functionalized POLY$_B$ segment (3400 MW PEG), having an aldehyde functional group at the terminus, via an amide linkage:

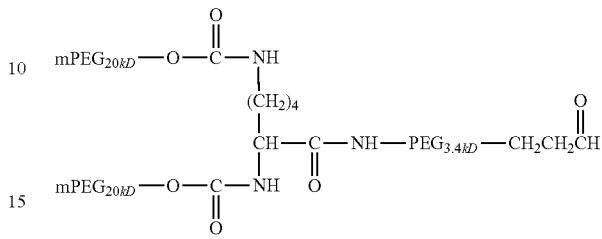

C. Forked Polymers

A "forked" polymer of the invention refers to a single segmented polymer (which can itself be, for example, linear or branched) which is linked to two functional groups, or, in a conjugate, to two pharmacologically active agents. See e.g. PCT Pubn. No. WO 99/45964. Certain forked polymers of the invention can be represented schematically as follows:

 (IIIa)

or

 (IIIb)

or

 (IIIc)

where POLY$_A$, POLY$_B$, X, and Y are as defined above; L represents a branched spacer group; and q is $\geq 2$, preferably 2 to about 100, more preferably 2 to about 10. In one embodiment, q is 2. Preferably, the branch point in the spacer group comprises a carbon atom (>CH—), though it may also comprise a nitrogen atom (>N—).

An exemplary forked polymer that may be represented by POLY$_A$-X-L-(POLY$_B$-Y)$_q$ (structure IIIb above) possesses the structure:

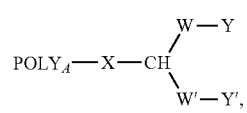

where W and W' are first and second tethering groups that can be the same or different, and comprise POLY$_B$ segments, connected to the branching atom, —CH, optionally via intervening spacer groups. In a particular embodiment, W and W' are identical.

A polymer of the invention may be forked as well as branched; for example, it may have the schematic structure (POLY$_A$)$_2$-L-X-L'-(POLY$_B$-Y)$_2$. L and L' may be the same or different. An exemplary structure of this type, having two maleimide functional groups, is:

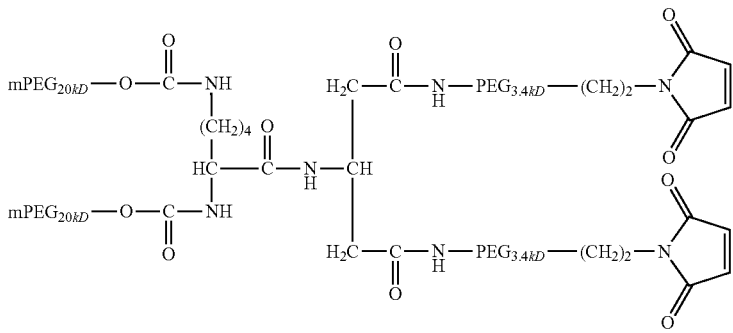

Preferably, in a forked PEG or a forked/branched PEG as illustrated above, where PEG$_A$ is mPEG and the functional group Y is a maleimide group, the segment PEG$_B$ has a molecular weight of at least 130, preferably at least 200, and more preferably at least 300. Alternatively, PEG$_B$ includes at least three, preferably at least four, and more preferably at least 10 monomeric PEG units.

Either POLY$_A$ or POLY$_B$ may also include pendant functional groups covalently attached along the length of the PEG backbone. The pendant reactive groups can be attached to the PEG backbone directly or through a spacer group, such as an alkylene group.

D. Multiarmed and Dendrimeric Polymers

A "multiarmed" polymer of the invention comprises three or more water-soluble polymer chains attached to a central core structure, and can be represented by the general structure:

$$M\text{-}\{POLY_A\text{-}X\text{-}(POLY_B\text{-}Y)_q\}_x \qquad (IV)$$

where M is a core structure, such as a polyol, having several linkage points for attachment of POLY$_A$, and x represents the number of "arms".

The value of x is less than or equal to the valence of the multivalent core structure, M. Typically, the value of x is equal to the valence of the core structure, M.

The value of x is typically 3 to about 100, more typically 3 to about 20. For example, a polyol core structure can generally provide from 3 to about 100 available hydroxy groups, and typically provides 3 to about 20, so that the branched polymer structure has from about 3 to about 100, more typically 3 to about 20, "arms". The core structure M is preferably selected from a polyol, a polyamine, and an amino acid whose side chain bears a functional group, and more preferably selected from a polyol and a polyamine. Types of suitable core structures are discussed further below.

In selected embodiments of structure (IV), q is 1 or 2; that is, each "arm" represents a linear polymer (q=1) or a "forked" polymer (q=2). In further embodiments, x is 3 to 20, or 3 to 10. Generally, q is 1, such that each POLY$_A$ is linked to a single POLY$_B$. However, q can be greater than 1, and POLY$_B$ can include more than one Y or a polyfunctional Y, as noted above. Where q is >1 or POLY$_B$ includes more than one Y, branched spacer groups, as represented by L above, are incorporated as appropriate. Generally, POLY$_B$ includes a single group Y.

The multiarmed polymer may also include some POLY$_A$ segments which are not further substituted. Accordingly, structure (IV) can represent a branched or dendritic polymer segment in which each of a plurality of POLY$_A$ polymer arms (where the plurality is equal to or less than q) is covalently attached to a POLY$_B$-Y segment via a covalent linkage, X.

The remaining POLY$_A$ polymer arms may be uncapped (i.e. hydroxyl terminated) or capped with a capping group such as described above, preferably an alkoxy group.

In selected embodiments, the multiarmed polymer is a PEG polymer, e.g.:

$$M\text{-}\{PEG_A\text{-}X\text{-}(PEG_B\text{-}Y)_q\}_x \qquad (IV')$$

where PEG$_A$ represents poly(ethylene glycol) comprising at least 4 and at most about 2000 —CH$_2$CH$_2$O— monomeric units, and PEG$_B$ represents poly(ethylene glycol) comprising at least 1 and at most about 120 —CH$_2$CH$_2$O— monomeric units, with the proviso that PEG$_B$ has a lower molecular weight than that of PEG$_A$. As above, the multiarmed polymer may also include some PEG$_A$ segments which are not further substituted. Accordingly, structure (IV') can represent a branched or dendritic polymer segment in which each of a plurality of PEG$_A$ polymer arms (where the plurality is equal to or less than q) is covalently attached to a PEG$_B$-Y segment via a covalent linkage, X. The remaining PEG$_A$ arms may be uncapped (i.e. hydroxyl terminated) or capped with a capping group such as described above, preferably an alkoxy group.

Since PEG$_A$ and PEG$_B$ are embodiments of POLY$_A$ and POLY$_B$, respectively, their preferred size and molecular weight ranges correspond to those described for POLY$_A$ and POLY$_B$ above. In selected embodiments, X comprises a carbamate, an amide, a carbonate, an ester, a urea, an amine, a thioether, or a disulfide. Preferably, X comprises a carbamate, an amide, a urea, or a carbonate.

Dendrimeric polymers of the invention comprise multiple (e.g., 3 to 50) water-soluble segmented polymers connected to a core structure. Such forms can be distinguished from "multi-armed" forms, where the "arms" are generally linear or moderately branched, in that dendrimeric polymers are very highly branched, with branching increasing with the distance from the core structure. Generally, each of a plurality (or all) of the arms will be linked to a POLY$_B$ segment and thence to a functional group Y.

D1. Core Structures

The core structure in multiarmed and dendrimeric polymers can be any group containing multiple linkage points for attachment of the polymer chains. Examples include polyols, polyamines, and amino acids having functional side chains. Of these, polyols and polyamines are preferred.

Polyols that are suitable for use as the polymer core are nearly limitless. Aliphatic polyols having from 1 to 10 carbon atoms and from 1 to 10 hydroxyl groups may be used, including ethylene glycol, other alkane diols, alkylidene alkyl diols, alkyl cycloalkane diols, alkane polyols such as glycerol or pentaerythritol, cycloalkylidene diols such as 1,5-decalindiol or 4,8-bis(hydroxymethyl) tricyclodecane, and the like. In one embodiment, branched polyols of the form HO—(CH(OH)CH$_2$O)$_n$H, prepared by condensation of glycerol, are employed.

Cycloaliphatic polyols may also be employed, including straight chained or closed-ring sugars and sugar alcohols, such as mannitol, sorbitol, inositol, xylitol, quebrachitol, threitol, arabitol, erythritol, adonitol, dulcitol, facose, ribose, arabinose, xylose, lyxose, rhamnose, galactose, glucose, fructose, sorbose, mannose, pyranose, altrose, talose, tagitose, pyranosides, sucrose, lactose, maltose, and the like. In general, any carbohydrate core, preferably a mono- or disaccharide, can be used, after reduction of aldehydes to hydroxyl groups, if desired.

Aromatic polyols may also be used as cores, particularly when a more hydrophobic core structure is desired. Suitable aromatic polyols include 1,1,1-tris(4'-hydroxyphenyl)alkanes, such as 1,1,1-tris(4-hydroxyphenyl)ethane, (1,3-adamantanediyl)diphenol, 2,6-bis(hydroxyalkyl)cresols, 2,2'alkylene-bis(6-t-butyl-4-alkylphenols),2,2'-alkylene-bis(t-butylphenols), catechol, alkylcatechols, pyrogallol, fluoroglycinol, 1,2,4-benzenetriol, resorcinol, alkylresorcinols, dialkylresorcinols, orcinol monohydrate, olivetol, hydroquinone, alkylhydroquinones, 1,1-bi-2-naphthol, phenyl hydroquinones, dihydroxynaphthalenes, 4,4'-(9-fluorenylidene)-diphenol, anthrarobin, dithranol, bis (hydroxyphenyl) methane biphenols, dialkylstilbesterols, bis(hydroxyphenyl)alkanes, bisphenol-A and derivatives thereof, meso-hexesterol, nordihydroguaiaretic acid, calixarenes and derivatives thereof, tannic acid, and the like.

Other core polyols that may be used include crown ethers, cyclodextrins, dextrins, and other carbohydrates such as starches and amylose. See also U.S. Pat. No. 5,932,462 (Harris et al., 1999), which is incorporated by reference herein in its entirety.

A large variety of polyamines are also available for use as core structures, including aliphatic diamines, triamines, tetramines, etc. Well known examples, some of which are naturally occurring, include α,ω-aliphatic diamines, e.g. 1,6-hexanediamine. Other diamines having diverse structures are commercially available; for example, 3-dimethylamino propylamine, 3-diethylaminopropylamine, N,N-dimethyl dipropylenetriamine, N,N'-di-t-butyl ethylenediamine, and bis(aminomethyl) tricyclododecane are available from Celanese Chemicals.

Aliphatic polyamines which are naturally occurring include spermidine (an aliphatic triamine) and spermidine (an aliphatic tetramine). Also useful as core structures are aliphatic polyamines, some of which include unsaturation and intervening cycloalkyl or aryl groups, reported for use as antiinfective agents in C. J. Bacchi et al., *Antimicrobial Agents and Chemotherapy* 46(1):55-61 (January 2002). These include tetramines of the form EtNH—R$^1$—NH—CH$_2$—R$^2$—CH$_2$—NH—R$_1$—NHEt, where each R' is n-butyl or cis-2-butenyl, and R$^2$ is selected from ethyl, cis-ethenyl, ethynyl, cyclopropyl (cis or trans), cyclobutyl (cis or trans), and ortho-phenyl. Also included are pentamines of the form Et-(NH—R$^1$)$_4$—NHR$^3$, where R$^1$ is again n-butyl or cis-2-butenyl and R$^3$ is ethyl, 2-hydroxyethyl or 2-aminoethyl. Also included are higher oligoamines of the form Et-(NHCH$_2$CH$_2$CH$_2$CH$_2$)$_{3-6}$-NH—R$^1$—(NHCH$_2$CH$_2$CH$_2$CH$_2$)$_{3-6}$-NHEt, where R' is again n-butyl or cis-2-butenyl.

E. Hydrogels

The water soluble polymers of the invention can also be used to form hydrogels, particularly crosslinked hydrogels (see U.S. Pat. No. 6,413,507, Bentley et al., 2002, which is incorporated herein by reference). Such gels, and conjugates based on these gels, are particularly useful for biocompatible controlled release dosage forms and wound dressings. Aqueous hydrogels can be used in various biomedical applications, such as soft contact lenses, wound management, drug delivery, and implants for tissue replacement and augmentation.

A crosslinked hydrogel of the invention comprises, in one embodiment, a water soluble segmented polymer as described herein, bonded to a crosslinking agent through a hydrolyzable linkage. The polymer has a functional group Y, such as an amino or hydroxyl group, available to react with the crosslinking agent to form a hydrolyzable linkage, such as a carbamate, carbonate or ester linkage. Preferably, the polymer has at least two such functional groups. In selected embodiments, the polymer comprises PEG segments. The functional groups are typically on POLY$_B$, but they may be present on POLY$_A$ or on both segments.

Accordingly, the polymer used to form the hydrogel can take one of the following forms:

or

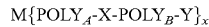

where X, Y, M, and x are as defined above.

The polymer is reacted with a crosslinking moiety which includes at least two groups effective to react with Y to form a covalent linkage.

The pharmacologically active agents to be delivered can be part of the crosslinking moiety of the hydrogel, or they can be incorporated in "prodrug" form by covalent linkage to the polymer backbone or to the crosslinking moiety. Agents to be delivered can also be loaded into the hydrogel during its synthesis, or afterwards, e.g., by diffusion into the cavity or matrix of the hydrogel, without being covalently bonded to the hydrogel structure.

The hydrogel can be used as a carrier for delivery of pharmacologically active agents, e.g. drugs, nutrients or labeling agents for imaging analysis, and for other suitable biomedical applications. For example, the hydrogel can carry therapeutic drugs and can be implanted or injected in the target area of the body.

Drugs which are physically trapped in the gel are released by diffusion as the gel degrades. Agents which are covalently bound through hydrolyzable linkages are released at a controllable rate as these linkages degrade. Because the hydrogel is characterized by the interconnection of a large number of hydrolytically degradable linkages, the degradation or breakdown of the hydrogel in the body is typically gradual in nature. Thus, it is particularly useful for sustained release of an agent in the body.

IV. Preparation of the Segmented Polymers

The invention includes methods of preparing the segmented water-soluble polymers. In general, a first water soluble polymer segment, such as that designated herein as POLY$_A$, having at least one functional group, Z, is provided, and is reacted with a second water soluble segment, such as that designated herein as POLY$_B$, having at least one functional group, Y', thereby covalently bonding the first and second segments by reaction of Z with Y'. Either POLY$_A$ or POLY$_B$, preferably POLY$_B$, comprises an additional functional group, Y, that is not readily reactive with either Z or Y' under the conditions of reaction of those two groups.

In general, the method and resulting functionalized polymer can be represented by:

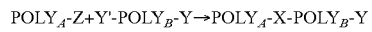

In selected embodiments, each of the first and second segments is a poly(alkylene) glycol), preferably a PEG. Typically, $POLY_A$ includes a capping group, such as an alkoxy or aryloxy group, at one terminus, and the functional group Z at the other terminus, and $POLY_B$ is heterobifunctional, having Y and Y' at its respective termini. When Y and Y' are different, a protecting strategy may be used that renders Y' reactive while Y remains unreacted.

The unreacting functional group Y can comprise any of the functional groups described herein, typically in protected form, as long as it is unreactive under the conditions of reaction of Z and Y'. These groups include, for example, nucleophiles such as hydroxyl, amino, hydrazine, hydrazide, or thio, and electrophiles such as carboxylic acids; carboxylic esters or carbonates, including imide esters or carbonates, imidazoyl ester or carbonate, and benzotriazole ester or carbonate; orthoesters; isocyanates; isothiocyanates; aldehydes, including glyoxal; ketones, including diones; thiones; alkenyl, including vinyl pyridine and vinyl sulfone; acrylate; methacrylate; acrylamide; sulfone; maleimide; disulfide, including orthopyridyl disulfide; halo, e.g. chloroethyl sulfone and iodoacetamide; epoxy, including glycidyl ether; sulfonate, including tosylate, mesylate, and tresylate; thiosulfonate; silane; alkoxysilane; halosilane; and phosphoramidate. These groups are provided in protected form if necessary. In a preferred embodiment, Y is a protected amino group, such that the segmented polymer has an amino group available for conjugation.

Generally, one of Z and Y' is a nucleophile, e.g. amine, hydrazine, hydrazide, thiol, or hydroxyl, and the other is an electrophilic group, e.g. N-succinimidyl carbonate, succinimidyl ester, benzotriazole carbonate, isocyanate, glycidyl ether, imidazolyl ester, p-nitrophenyl carbonate, aldehyde, maleimide, ortho-pyridyl disulfide, acrylate, or vinyl sulfone. See, for example, the discussion of functional groups provided above. The nucleophilic group may be present on either the $POLY_A$ or the $POLY_B$ segment, with a corresponding electrophilic group present on the $POLY_B$ or $POLY_A$ segment, respectively. Any of these groups can be provided in protected form on the starting polymer segments and deprotected prior to reaction or in situ. See, for example, the working Examples provided below. Typical reaction schemes include reaction of an amine, on either $POLY_A$ or $POLY_B$, with an activated ester, carbonate, or isocyanate, to form an amine, carbamate, or urea linkage, respectively. One preferred strategy, as illustrated in the working Examples below, employs the reaction of either an NHS ester or a benzotriazolyl carbonate (as group Z on $POLY_A$) with an amine (as group Y' on $POLY_B$) to form a carbamate or amide as the linkage X. Embodiments of Y illustrated in these Examples include thiosulfonate, carboxylic acid, carboxylic ester, amine, aldehyde or protected aldehyde (acetal), and maleimide.

These strategies can be readily adapted for preparation of other structural types, such as branched, forked, or multi-arm polymers. For example, in a typical preparation of a branched polymer of the general form:

$(POLY_A\text{-}X\text{-}POLY_B)_q\text{-}L\text{-}Y$ such as described in Section IIIA above, a compound having the structure $(Z')_q\text{-}L\text{-}Y$ is reacted with $Y'\text{-}POLY_B\text{-}Z''$, where Z' and Z" are effective to form linkages between each $POLY_B$ and the spacer group, and Y and Y' are unreactive under the conditions of this reaction, or are in protected form during the reaction. The resulting structure, $(Y'\text{-}POLY_B)_q\text{-}L\text{-}Y$, is then reacted with $POLY_A\text{-}Z$ as described above. Generally, q is 2.

In a typical preparation of a segmented multi-arm polymer, such as described in Section IIIB above, a $POLY_A$ segment, such as a PEG segment having a molecular weight in the ranges described above for $POLY_A$, is attached to each linkage point on the core structure, e.g. each hydroxyl group of a polyol. These attachments may be via spacer groups or, more preferably, direct linkages. The free terminus of each $POLY_A$ "arm" is then converted, if necessary, to a functional group Z, prior to combination with a $POLY_B$ segment, such as a PEG segment having a molecular weight in the ranges described above for $POLY_B$, having a reactive group Y'. Preferably, the $POLY_B$ segments, or at least a plurality of the $POLY_B$ segments, are heterobifunctional, as described above, so that a functional group Y remains at the free terminus of at least a plurality of the $POLY_B$ segments in the resulting multi-arm segmented polymer. Again, the functional group(s) Y may be in protected form.

As noted above, the segmented water soluble polymers can be prepared with one or more weak or degradable linkages in the polymer backbone, such as a poly(alkylene glycol) having periodic ester linkages in the polymer backbone. Other hydrolytically or enzymatically cleavable linkages include carbonates, carbamates, and hydrazones. Some amides may also be degraded in vivo by peptidases. The introduction of one or more degradable linkages into the polymer chain can provide additional control over the final desired pharmacological properties of the conjugate upon administration. For example, a large and relatively inert conjugate (i.e., having one or more high molecular weight PEG chains attached thereto, for example, one or more PEG chains having a molecular weight greater than about 8,000, wherein the conjugate possesses little bioactivity) may be administered, and upon hydrolysis in vivo generates a bioactive conjugate possessing a smaller portion of the original PEG chain. In this way, the properties of the conjugate can be more effectively tailored to balance the bioactivity of the conjugate over time. The polymers may also be used in the fabrication of in vivo degradable solid dosage forms of the conjugated agent.

The linking reactions generally involve known reactions and are carried out according to standard methods of organic synthesis, particularly polymer modification methods. See, for example, the working examples provided herein. Suitable solvents typically include, but are not limited to, tetrahydrofuran, dioxane, acetonitrile, methylene chloride, chloroform, dimethylformamide, dimethylsulfoxide, and, for less polar materials, benzene, toluene, xylenes, and petroleum ether.

As discussed above, it has been found that the modified and/or conjugated low molecular weight $POLY_B$ segments undergo synthetic operations such as dissolution, filtration, separation, and purification with more efficiency and higher yields than similarly modified and/or conjugated high molecular weight polymers. In general, it is easier to separate mixtures of low molecular weight polymers into component species than similar higher weight polymers. End group modification and conjugation is generally a multi-step process, with each step of the functionalization resulting in polymeric impurities. If purification is ineffective, which can be the case when dealing with high molecular weight polymers, the impurities accumulate throughout functionalization of the polymer to an unacceptable level. By first performing functionalization and purification processes on a low molecular weight polymer and subsequently joining the purified low molecular weight polymer with a high molecular weight polymer, in accordance with this invention, process steps involving the high molecular weight polymer are minimized, resulting in a high molecular weight functionalized or conjugated polymer derivative in overall desirable purity and yield. Accordingly, it is preferred, in synthesizing the subject polymers, that the step of linking the functionalized $POLY_B$ segment(s) with the higher molecular weight POLY$_A$ segment is carried out near or at the end of the synthetic scheme.

V. Preparation of Conjugates

In another embodiment of the invention, a method for preparing a polymer conjugate is provided. The method comprises the step of contacting a water soluble, segmented polymer as described herein, having at least one functional group Y, with a pharmacologically active agent having a corresponding reactive group Z', under suitable condition to produce a covalent linkage between Y and Z'. Y is frequently an electrophilic group and Z' a nucleophilic group, though these roles may be reversed. Examples of suitable pharmacologically active agents are discussed below.

The specific conditions for effecting conjugation depend, in part, on the functional group(s) Y present on the segmented polymer, the molecular weight of the polymer, and the reactive group(s) Z' present in the specific pharmacologically active agent, as well as the possible presence of additional reactive functional groups within the agent. For any given polymer and pharmacologically active agent, however, suitable reaction conditions, including protection strategies if necessary, will be known to one of ordinary skill in the art or can be identified through routine experimentation. Such conditions include pH, temperature, reagent concentration, and so forth.

For example, when the polymer contains an N-hydroxysuccinimide active ester (e.g., succinimidyl succinate, succinimidyl propionate, or succinimidyl butanoate), and the active agent contains an amine group (e.g., a terminal or side chain amine group on a polypeptide), conjugation can be effected at a pH of from about 7.5 to about 9.5 at room temperature, to form an amide linkage. In analogous reactions, reaction of an amine with an activated carbonate (e.g. succinimidyl or benzotriazyl carbonate) forms a carbamate linkage, and reaction of an amine with an isocyanate (R—N=C=O) forms a urea linkage (R—NH—(C=O)—NH—R').

In further embodiments, when the polymer contains a vinyl sulfone or maleimide (see e.g. U.S. Pat. No. 5,739,208; PCT Pubn. WO 01/62827), and the pharmacologically active agent contains a thiol group (as in a cysteine side chain on a polypeptide or protein), conjugation can be effected at a pH of from about 7 to about 8.5 at room temperature, to form a sulfide (thioether) linkage.

Alternatively, when the functional group Y comprises an aldehyde, a ketone, a hydrate thereof, an acetal or ketal, or a hemiacetal or hemiketal, and the pharmacologically active agent contains a primary amine, conjugation can be effected by reductive amination, where the initially formed imine bond is reduced to the amine with a suitable reducing agent such as NaCNBH$_3$. Such reactions can also be carried out with the sulfur analogs of these functional groups.

Conversely, in the reactions described above, the polymer may contain the nucleophilic functional group, for reaction with an electrophilic group on the agent to be attached. As another example, an amine- or hydrazide-modified polymer can be used for conjugation to a carbohydrate-containing compound, such as a saccharide, a glycolipid or a glycoprotein, where the carbohydrate residue is first treated with periodate to generate reactive aldehyde groups.

Other types of bonds formed by such conjugation are described above. For additional information concerning such conjugation reactions, reference is made to Hermanson, BIOCONJUGATE TECHNIQUES, Academic Press, 1996. Several working examples of conjugation are also provided below in the Examples section.

The molecular weight and architecture of the water soluble polymer (including the number of available functional groups per a given molecular weight of polymer) can be selected based on the drug being delivered and condition being treated. For example, long circulating time is a known benefit of higher molecular weight polymer conjugates. However, in some cases, as in administering thrombolytics, long circulating time may be undesirable. The use of a lower molecular weight polymer can also reduce the overall weight of the composition for a given dose of the active agent, and may be less likely to block an active site on the agent.

Preferably, conjugates having a stable linkage (e.g., an amine or ether linkage) between the polymer and the active agent will possess, in conjugate form, at least some degree of the bioactivity of the unmodified agent. The conjugates can also be designed as prodrugs, such that the covalent linkage between the segmented polymer and the pharmacologically active agent is degradable in vivo, to allow release of the agent. Exemplary degradable linkages include carboxylate esters, phosphate esters, thioesters, anhydrides, acetals, ketals, acyloxyalkyl ethers, imines, hydrazones (typically formed by reaction of a hydrazide and an aldehyde), disulfides, and orthoesters (formed by reaction between a formate and an alcohol). Linkages can often be tailored to control the rate of cleavage, for example, by modifying the substitution on an ester linkage. Other examples include linkages designed such that cleavage is intramolecularly accelerated by a neighboring group, such as an amine, or the "benzyl elimination" system, involving cleavage of a benzyl disulfide (e.g. M. Wakselman, *Nouveau J. de Chemie* 7:439-447, 1983).

VI. Pharmacologically Active Agents

The polymers of the invention can be conjugated to any pharmacologically active agent which has a suitable functional group for attachment, for the purpose of improving the pharmacological properties (such as solubility, biodistribution, rate of delivery, or metabolism) of the agent. The active agent is frequently a therapeutically active agent, i.e. a drug, but it may also include diagnostic agents, including antibodies or other binding moieties, or dyes or other imaging materials, as well as targeting or delivery agents, e.g. molecules for targeting specific receptors.

The active agent may fall into one of a number of structural classes, including but not limited to small molecules (including difficultly soluble or insoluble small molecules), peptides, polypeptides, proteins, polysaccharides, steroids, nucleotides, oligonucleotides, polynucleotides, lipids, fats, electrolytes, and the like.

Biologically or therapeutically active agents to be conjugated to segmented, water soluble polymer of the invention may be any one or more of the following. Suitable agents may be selected from, for example, hypnotics and sedatives, psychic energizers, tranquilizers, respiratory drugs, anticonvulsants, muscle relaxants, antiparkinson agents (dopamine antagonists), analgesics, anti-inflammatories, antianxiety drugs (anxiolytics), appetite suppressants, antimigraine agents, muscle contractants, anti-infectives (antibiotics, antivirals, antifungals, vaccines) antiarthritics, antimalarials, antiemetics, anepileptics, bronchodilators, cytokines, growth factors, anti-cancer agents, antithrombotic agents, antihypertensives, cardiovascular drugs, antiarrhythmics, antioxicants, anti-asthma agents, hormonal agents including contraceptives, sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents.

Specific examples of active agents suitable for covalent attachment to a polymer of the invention include but are not limited to aspariginase, amdoxovir (DAPD), antide, becaplermin, calcitonins, cyanovirin, denileukin diftitox, erythropoietin (EPO), EPO agonists (e.g., peptides from about 10-40 amino acids in length and comprising a particular core sequence as described in WO 96/40749), dornase alpha, erythropoiesis stimulating protein (NESP), coagulation factors such as Factor VIIa, Factor VIII, Factor IX, von Willebrand factor; ceredase, cerezyme, alpha-glucosidase, collagen, cyclosporin, alpha defensins, beta defensins, exedin-4, granulocyte colony stimulating factor (GCSF), thrombopoietin (TPO), alpha-1 proteinase inhibitor, elcatonin, granulocyte macrophage colony stimulating factor (GMCSF), fibrinogen, filgrastim, growth hormones human growth hormone (hGH), growth hormone releasing hormone (GHRH), GRO-beta, GRO-beta antibody, bone morphogenic proteins such as bone morphogenic protein-2, bone morphogenic protein-6, OP-1; acidic fibroblast growth factor, basic fibroblast growth factor, CD-40 ligand, heparin, human serum albumin, low molecular weight heparin (LMWH), interferons such as interferon alpha, interferon beta, interferon gamma, interferon omega, interferon tau; interleukins and interleukin receptors such as interleukin-1 receptor, interleukin-2, interluekin-2 fusion proteins, interleukin-1 receptor antagonist, interleukin-3, interleukin-4, interleukin-4 receptor, interleukin-6, interleukin-8, interleukin-12, interleukin-13 receptor, interleukin-17 receptor; lactoferrin and lactoferrin fragments, luteinizing hormone releasing hormone (LHRH), insulin, pro-insulin, insulin analogues (e.g., mono-acylated insulin as described in U.S. Pat. No. 5,922,675), amylin, C-peptide, somatostatin, somatostatin analogs including octreotide, vasopressin, follicle stimulating hormone (FSH), influenza vaccine, insulin-like growth factor (IGF), insulintropin, macrophage colony stimulating factor (M-CSF), plasminogen activators such as alteplase, urokinase, reteplase, streptokinase, pamiteplase, lanoteplase, and teneteplase; nerve growth factor (NGF), osteoprotegerin, platelet-derived growth factor, tissue growth factors, transforming growth factor-1, vascular endothelial growth factor, leukemia inhibiting factor, keratinocyte growth factor (KGF), glial growth factor (GGF), T Cell receptors, CD molecules/antigens, tumor necrosis factor (TNF), monocyte chemoattractant protein-1, endothelial growth factors, parathyroid hormone (PTH), glucagon-like peptide, somatotropin, thymosin alpha 1, thymosin alpha 1 IIb/IIIa inhibitor, thymosin beta 10, thymosin beta 9, thymosin beta 4, alpha-1 antitrypsin, phosphodiesterase (PDE) compounds, VLA-4 (very late antigen-4), VLA-4 inhibitors, bisphosponates, respiratory syncytial virus antibody, cystic fibrosis transmembrane regulator (CFTR) gene, deoxyreibonuclease (Dnase), bactericidal/permeability increasing protein (BPI), and anti-CMV antibody. Exemplary monoclonal antibodies include etanercept (a dimeric fusion protein consisting of the extracellular ligand-binding portion of the human 75 kD TNF receptor linked to the Fc portion of IgG1), abciximab, afeliomomab, basiliximab, daclizumab, infliximab, ibritumomab tiuexetan, mitumomab, muromonab-CD3, iodine 131 tositumomab conjugate, olizumab, rituximab, and trastuzumab (herceptin).

Additional agents suitable for covalent attachment to a polymer of the invention include but are not limited to amifostine, amiodarone, aminoglutethimide, amsacrine, anagrelide, anastrozole, asparaginase, anthracyclines, bexarotene, bicalutamide, bleomycin, buserelin, busulfan, cabergoline, capecitabine, carboplatin, carmustine, chlorambucin, cisplatin, cladribine, clodronate, cyclophosphamide, cyproterone, cytarabine, camptothecins, 13-cis retinoic acid, all trans retinoic acid; dacarbazine, dactinomycin, daunorubicin, dexamethasone, diclofenac, diethylstilbestrol, docetaxel, doxorubicin, epirubicin, estramustine, etoposide, exemestane, fexofenadine, fludarabine, fludrocortisone, fluorouracil, fluoxymesterone, flutamide, gemcitabine, epinephrine, L-Dopa, hydroxyurea, idarubicin, ifosfamide, imatinib, irinotecan, itraconazole, goserelin, letrozole, leucovorin, levamisole, lomustine, mechlorethamine, medroxyprogesterone, megestrol, melphalan, mercaptopurine, methotrexate, metoclopramide, mitomycin, mitotane, mitoxantrone, naloxone, nicotine, nilutamide, octreotide, oxaliplatin, pamidronate, pentostatin, pilcamycin, porfimer, prednisone, procarbazine, prochlorperazine, ondansetron, raltitrexed, sirolimus, streptozocin, tacrolimus, tamoxifen, temozolomide, teniposide, testosterone, tetrahydrocannabinol, thalidomide, thioguanine, thiotepa, topotecan, tretinoin, valrubicin, vinblastine, vincristine, vindesine, vinorelbine, dolasetron, granisetron; formoterol, fluticasone, leuprolide, midazolam, alprazolam, amphotericin B, podophylotoxins, nucleoside antivirals, aroyl hydrazones, sumatriptan; macrolides such as erythromycin, oleandomycin, troleandomycin, roxithromycin, clarithromycin, davercin, azithromycin, flurithromycin, dirithromycin, josamycin, spiromycin, midecamycin, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, grepafloxacin, gatifloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin; aminoglycosides such as gentamicin, netilmicin, paramecin, tobramycin, amikacin, kanamycin, neomycin, and streptomycin, vancomycin, teicoplanin, rampolanin, mideplanin, colistin, daptomycin, gramicidin, colistimethate; polymixins such as polymixin B, capreomycin, bacitracin, penems; penicillins including penicllinase-sensitive agents like penicillin G, penicillin V; penicllinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefmetazole, ceftazidime, loracarbef, and moxalactam, monobactams like aztreonam; and carbapenems such as imipenem, meropenem, pentamidine isethiouate, albuterol sulfate, lidocaine, metaproterenol sulfate, beclomethasone diprepionate, triamcinolone acetamide, budesonide acetonide, fluticasone, ipratropium bromide, flunisolide, cromolyn sodium, and ergotamine tartrate; taxanes such as paclitaxel; SN-38, and tyrphostines.

The above exemplary biologically active agents are meant to encompass, where applicable, analogues, agonists, antagonists, inhibitors, isomers, and pharmaceutically acceptable salt forms thereof. In reference to peptides and proteins, the invention is intended to encompass synthetic, recombinant, native, glycosylated, non-glycosylated, and biologically active fragments and analogs thereof.

The segmented, water soluble polymers of the invention may employed in various useful conjugates known in the art;

for example, PEG-derivatized lipids for use in long-circulating liposomes (see e.g. D. Lasic and F. Martin, STEALTH LIPOSOMES, CRC Press, Boca Raton, Fla., 1995). Such lipids include phospholipids, such as various phosphatidyl ethanolamines, and are typically attached to the functionalized water soluble polymer, such as a segmented PEG having an electrophilic functional group, via an amine or hydroxyl group on the polar head group of the phospholipid.

Yet another useful conjugate is a PEG-biotin conjugate. Such a compound can serve as a tether in binding of moieties via the well known noncovalent biotin-avidin association. A heterobifunctional segmented polymer of the invention, having a biotin at one terminus and a functional group, as described above, at the other terminus, can be used to tether biotin to any desired molecule or surface having a corresponding functional group; the resulting conjugates can then be bound to avidin-containing molecules or surfaces.

The reactive polymers of the invention may also be attached, either covalently or non-covalently, to various solid entities, including chemical separation and purification surfaces, solid supports for synthesis, or metal surfaces. One type of functionalized polymer that is especially useful for attachment to surfaces is silylated PEG, for example, PEG terminated with a trialkoxysilyl group (see e.g. S. Jo et al., *Biomaterials* 21(6):605-16, 2000). Such groups form covalent siloxane bonds to surfaces bearing hydroxyl or oxide groups, such as glass or metals having metal oxide at the surface.

The degree of absorption of cells and proteins to PEG, in comparison .to other synthetic materials, is very low (G. Hooftman et al., *J. Bioact. Compat. Pol.* 11:135, 1996), which is consistent with its low immunogenicity. Accordingly, surfaces coated with the water-soluble, biocompatible polymers of the invention can be used, for example, in arterial replacements and other medical and diagnostic devices. The polymers of the invention may also be employed in biochemical sensors, bioelectronic switches, and gates.

VII. Pharmaceutical Compositions and Methods of Administration

The invention also provides pharmaceutical preparations comprising a conjugate as provided herein in combination with a pharmaceutical excipient. Generally, the conjugate itself will be in solid form, and is combined with a suitable pharmaceutical excipient that can be in either solid or liquid form.

Exemplary excipients include, without limitation, carbohydrates, inorganic salts, antimicrobial agents, antioxidants, surfactants, buffers, acids, bases, and combinations thereof. A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The preparation may also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the preparation as well. Antioxidants are used to prevent oxidation, thereby preventing the deterioration of the conjugate or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant may be present as an excipient. Exemplary surfactants include: polysorbates, such as "Tween 20" and "Tween 80," and pluronics such as F68 and F88 (both available from BASF, Mount Olive, N.J.); sorbitan esters; lipids, such as phospholipids such as lecithin and other phosphatidyl cholines, phosphatidyl ethanolamines (although preferably not in liposomal form), fatty acids and fatty esters; steroids, such as cholesterol; and chelating agents, such as EDTA, zinc and other such suitable cations.

Acids or bases may be present as an excipient in the preparation. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumarate, and combinations thereof.

The amount of the conjugate in the composition will vary depending on a number of factors, but will optimally be a therapeutically effective dose when the composition is stored in a unit dose container (e.g., a vial). In addition, the pharmaceutical preparation can be housed in a syringe. A therapeutically effective dose can be determined experimentally by repeated administration of increasing amounts of the conjugate in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then further exploring the range at which optimal performance is attained with no significant adverse effects. Generally, however, the excipient will be present in the composition in an amount of about 1% to about 99% by weight, preferably from about 5%-98% by weight, more preferably from about 15-95% by weight of the excipient, with concentrations less than 30% by weight most preferred.

The foregoing pharmaceutical excipients, along with other excipients, are described in "Remington: The Science & Practice of Pharmacy", $19^{th}$ ed., Williams & Williams, (1995), the "Physician's Desk Reference", $52^{nd}$ ed., Medical Economics, Montvale, N.J. (1998), and Kibbe, A. H., "Handbook of Pharmaceutical Excipients", $3^{rd}$ Edition, American Pharmaceutical Association, Washington, D.C., 2000.

The pharmaceutical compositions encompass various formulations, preferably those suited for injection, e.g., suspensions and solutions as well as powders that can be reconstituted. The pharmaceutical compositions can also take other forms such as syrups, creams, ointments, tablets, powders, and the like. Modes of administration include administration by injection, e.g. parenteral, intravenous, intraarterial, intramuscular, subcutaneous, and intrathecal, as well as pulmonary, rectal, transdermal, transmucosal, and oral delivery.

Suitable formulation types for parenteral administration include ready-for-injection solutions, dry powders for combination with a solvent prior to use, suspensions ready for injection, dry insoluble compositions for combination with a vehicle prior to use, emulsions and liquid concentrates for dilution prior to administration.

The invention also provides a method for administering a conjugate as provided herein to a patient suffering from a condition, or prone to a condition, that is responsive to treatment or prevention with the conjugate. The method comprises administering, e.g. via injection, a therapeutically effective amount of the conjugate, preferably provided as part of a pharmaceutical preparation as described above.

The dose to be administered, both unit dosage and dosing schedule, will vary depend upon the age, weight, and general condition of the subject, as well as the severity of the condition being treated, the judgment of the health care professional, and the agent being administered. Therapeutically effective amounts are known to those skilled in the art and/or are described in the pertinent reference texts and literature. Generally, a therapeutically effective amount of a conjugate will range from about 0.001 mg to 100 mg, preferably in doses from 0.01 mg/day to 75 mg/day, and more preferably in doses from 0.10 mg/day to 50 mg/day. Exemplary dosing schedules include, for example, one to five times a day, one to three times weekly, or one or two times monthly. Once the clinical endpoint has been achieved, dosing of the composition is halted.

In some embodiments described herein, the segmented polymer conjugate contains cleavable linkages, which may include the linkage(s) between the $POLY_A$ and $POLY_B$ segments. This can be advantageous when, for example, clearance from the body is potentially a problem because of the size of the conjugate. Optimally, clearance of the conjugate (via cleavage of individual water-soluble polymer portions) can be modulated by selecting the polymer molecular size and the type and frequency of degradable linkage that provides the desired clearance properties. One of ordinary skill in the art can determine, using routine experimentation, a proper molecular size and cleavable functional group, e.g. by first preparing a series of polymers and/or conjugates with different molecular weights and cleavable linkages, and then obtaining a clearance profile by administering the compound to a patient and taking periodic blood and/or urine samples. Once a clearance profile has been obtained for each tested conjugate, a suitable conjugate can be identified.

EXAMPLES

The following examples illustrate but are not intended in any way to limit the invention.

Examples 1 and 2 demonstrate the conversion of the functional group (Y) of a low MW ("$POLY_B$") polymer from hydroxy to mesylate (methanesulfonate) and p-toluenethiosulfonate, respectively, in good yield.

Example 1

Synthesis of α-t-Boc amino-ω-methanesulfonate PEG(3400)

BocNH-PEG$_{3.4kD}$-OMs

α-N-t-Boc amino-ω-hydroxy PEG(3400) (MW 3318 Da, 4.0 g, 0.0012 mol) (Shearwater Corp.) was azeotroped in chloroform (80 ml) on a rotary evaporator at 35° C. to dryness, and chloroform (50 ml) was added to the residual syrup. The solution was cooled to 4° C. under argon, and triethylamine (0.31 ml, 0.0022 mol) was injected, followed by slow injection of methanesulfonyl chloride (0.15 ml, 0.0019 mol). The reaction mixture was stirred overnight under argon while the bath was allowed to rise to ambient temperature. Anhydrous sodium carbonate (4.0 gm) was added to the reaction mixture, and the resulting solution was stirred at room temperature for one hour. The mixture was then filtered, and the filtrate was concentrated to dryness. Isopropanol (40 ml) was added, and the precipitated product was collected by filtration and dried under vacuum to yield 3.7 g α-t-Boc amino-ω-methanesulfonate PEG(3400). NMR (DMSO-d6): 1.37 ppm (s, —OC(CH$_3$)$_3$), 3.51 ppm (s, PEG backbone), 4.31 ppm (t, —CH$_2$SO$_2$—), 6.76 ppm (—CH$_2$NH—CO—).

Example 2

Synthesis of α-t-Boc amino-ω-p-toluenethiosulfonate PEG(3400)

BocNH-PEG$_{3.4kD}$-STs

α-t-Boc amino-ω-methanesulfonate PEG(3400) (the product of Example 1) (1.0 g, 0.30 mmol) was azeotroped to dryness in chloroform (30 ml) on a rotary evaporator at 35° C., and anhydrous ethanol (15 ml) was added to the residual syrup. Potassium p-toluenethiosulfonate (292 mg, 1.25 mmol) was added, and the mixture was refluxed under argon overnight. The solvent was removed on a rotary evaporator at 40° C., and the residue was dried under vacuum for 30 minutes. The crude product was dissolved in 100 ml 1M NaH$_2$PO$_4$—Na$_2$HPO$_4$ buffer solution (contain 10 wt % NaCl) at pH 5.8, and the resulting solution was extracted with dichloromethane (100 ml×3). The dichloromethane phase was dried over anhydrous sodium sulfate, filtered, and the filtrate concentrated to near dryness on a rotary evaporator. The product was precipitated by addition of isopropanol/ether (40 ml/20 ml), collected by filtration, and dried under vacuum. Yield: 0.7 g α-t-Boc amino-ω-p-toluenethiosulfonate PEG(3400). NMR: (DMSO-d6): 1.37 ppm (s, —OC(CH$_3$)$_3$), 2.43 ppm (s, CH$_3$—CH$_2$=CH$_2$/Ar), 3.51 ppm (s, PEG backbone), 6.76 ppm (t, —CH$_2$NH—CO—), 7.49 ppm (dd, CH$_3$—CH$_2$=CH$_2$/Ar), 7.82 ppm (dd, CH$_3$—CH$_2$=CH$_2$/Ar).

Example 3 demonstrates the deprotection of the amino group of the low molecular weight ("$POLY_B$") polymer of Example 2 in good yield.

Example 3

Synthesis of α-NH$_2$-ω-p-toluenethiosulfonate PEG (3400)

H$_2$N-PEG$_{3.4kD}$-STs

α-t-Boc amino-ω-p-toluenethiosulfonate PEG(3400) (the product of Example 2) (0.7 g) was dissolved in anhydrous dichloromethane (3.5 ml) and trifluroacetic acid (3.5 ml) under argon. The solution was stirred at room temperature for one hour and concentrated to dryness. Isopropanol (20 mL) was added, and the precipitated product was collected by filtration and dried under vacuum. Yield: 0.6 g α-NH$_2$-ω-p-toluenethiosulfonate PEG(3400). NMR (DMSO-d6): 2.43 ppm (s, CH$_3$—CH$_2$=CH$_2$/Ar), 2.95 ppm (t, —OCH$_2$CH$_2$NH$_2$), 3.51 ppm (s, PEG backbone), 7.49 ppm (dd, CH$_3$—CH$_2$=CH$_2$/Ar), 7.82 ppm (dd, CH$_3$—CH$_2$=CH$_2$/Ar).

Example 4 demonstrates the linking of a high molecular weight ("POLY$_A$") and low molecular weight ("POLY$_B$") polymer, by reaction of an amine on POLY$_B$ with a benzotriazole carbonate on POLY$_A$, to form a functionalized, segmented carbamate-linked polymer. The segmented polymer product has a p-toluenethiosulfonate functionality (from the POLY$_B$ segment).

Example 4

Synthesis of mPEG(23.4 kDa)-p-toluenethiosulfonate

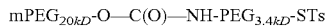

MPEG(20 kDa)-1-benzotriazole carbonate (813 mg, MW 21 kDa, 0.039 mmol) (Shearwater Corp.) and PEG(3400)-α-NH$_2$-ω-p-toluenethiosulfonate (the product of Example 3) (MW 3805 Da, 200 mg, 0.053 mmol) were dissolved in anhydrous dichloromethane (20 ml) under argon, and triethylamine (30.8 μl, 0.22 mmol) was injected. The solution was stirred at room temperature overnight, then concentrated to dryness. Isopropanol (10 ml) was added, and the precipitated product was collected by filtration and dried under vacuum. Yield: 843 mg.

The crude mPEG (23.4 kDa)-p-toluenethiosulfonate (560 mg) in 50 mL deionized water was loaded onto a column packed with 50 ml Poros® media. The column was eluted with 100 ml de-ionized water. Sodium chloride (15 g) was added to the eluant, and the resulting solution was extracted with dichloromethane (100 ml×3). The extract was dried over anhydrous sodium sulfate, filtered, and the filtrate concentrated to near dryness on a rotary evaporator. Ethyl ether (50 ml) was added to precipitate the product. The product was collected by filtration and dried under vacuum. Yield 495 mg mPEG(23.4 kDa)-p-toluenethiosulfonate. NMR (DMSO-d6): 2.43 ppm (s, CH$_3$—CH$_2$=CH$_2$/Ar), 3.51 ppm (s, PEG backbone), 7.23 ppm (t, —NHCOO—), 7.49 ppm (dd, CH$_3$—CH$_2$=CH$_2$/Ar), 7.82 ppm (dd, CH$_3$—CH$_2$=CH$_2$/Ar).

Example 5 demonstrates the conjugation of a biologically active agent, α1-antitrypsin, with the segmented polymer derivative of Example 4, via the functional group p-toluenethiolsulfonate.

Example 5

PEGylation of α1-antitrypsin

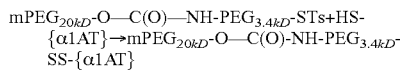

To a solution of α1-antitrypsin (1 mg, Sigma, MW 25 kDa) in 100 mM sodium phosphate (pH 7.2, 1 ml) was added 2.8 mg of mPEG p-toluenethiolsulfonate (the product of Example 4) (24 kDa), and the solution was stirred overnight at room temperature. Capillary electrophoresis indicated that the PEG α1-antitrypsin conjugate was formed in 36% yield. SDS gel electrophoresis also demonstrated the presence of the PEG conjugate. Treatment of the PEG conjugate with β-mercaptoethanol resulted in the formation of α1-antitrypsin, as evidenced by gel electrophoresis, thus indicating the presence of a disulfide linkage in the PEG α1-antitrypsin conjugate.

Example 6 provides another illustration of the linking of a high molecular weight ("POLY$_A$") and low molecular weight ("POLY$_B$") polymer, by reaction of an amine on POLY$_B$ with a benzotriazole carbonate on POLY$_A$, to form a functionalized, segmented carbamate-linked polymer. In this case, the segmented polymer product has a carboxylic acid functionality (from the POLY$_B$ segment).

Example 6 mPEG(22 KDa)-propionic acid

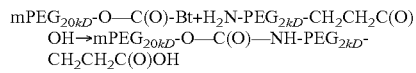

To a solution of mPEG(20 KDa)-benzotriazole carbonate (2.0 g, 0.1 mmol) (Shearwater Corporation) in methylene chloride (20 ml) were added PEG(2 KDa)-α-amino-ω-propionic acid (0.24 g, 0.12 mmol) (Shearwater Corporation) and triethylamine (0.06 ml), and the reaction mixture was stirred overnight at room temperature under argon. The mixture was filtered and evaporated to dryness. The crude product was dissolved in methylene chloride and precipitated with isopropyl alcohol, and the precipitate was dried under reduced pressure. Yield 1.9 g. NMR (d$_6$-DMSO): 2.44 ppm (t, —CH$_2$—COO—), 3.11 ppm (q, —CH$_2$_NH—), 3.24 ppm (s, —OCH$_3$), 3.51 ppm (s, PEG backbone), 4.04 ppm (m, —CH$_2$_O(C=O)—), 7.11 ppm (t, —(C=O)—NH—). Anion exchange chromatography yielded mPEG(22 KDa)-propionic Acid (93%) and mPEG-20 KDa (7%).

Example 7 demonstrates the conversion of the functional group, Y, of the segmented polymer produced in Example 6 from propionic acid to propionic acid N-hydroxysuccinimide ester.

Example 7 mPEG(22 KDa)-propionic acid N-hydroxysuccinimide ester

To a solution of mPEG(22 KDa)-propionic acid (the product of Example 6) (1.1 g, 0.050 mmol) in anhydrous methylene chloride (10 ml), N-hydroxysuccinimide (0.0063 g, 0.055 mmol) was added, followed by 1,3-dicyclohexylcarbodiimide (1.0 M solution in methylene chloride, 0.05 ml, 0.055 mmol). The reaction mixture was stirred overnight at room temperature under argon. The mixture was filtered and the solvent was evaporated. The crude product was dissolved in methylene chloride, precipitated with isopropyl alcohol, and dried under reduced pressure. Yield 0.9 g. NMR (d$_6$-DMSO): 2.81 ppm (s, —CH$_2$—CH$_2$— (succinate)), 2.92 ppm (t, —CH$_2$—COO—), 3.11 ppm (q, —CH$_2$—NH—), 3.24 ppm (s, —OCH$_3$), 3.51 ppm (s, PEG backbone), 4.03 ppm (m, —CH$_2$—O(C=O)—), 7.11 ppm (t, (C=O)—NH—).

Example 8 demonstrates the conversion of the functional group (Y) of a low MW ("POLY$_B$") polymer from propionic acid to methyl propionate.

Example 8

PEG(2 KDa)-α-amino-ω-propionic acid methyl ester

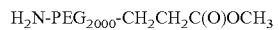

To a solution of PEG(2 KDa)-α-amino-ω-propionic acid (10 g, 0.0050 mol) (Shearwater Corporation) in anhydrous methylene chloride (100 ml), 1-hydroxybenzotriazole (0.30 g), 4-(dimethylamino)pyridine (1.0 g), methanol (3.2 g, 0.100 mol) and 1,3-dicyclohexylcarbodiimide (1.0 M solution in methylene chloride, 7.5 ml, 0.0075 mol) were added. The reaction mixture was stirred overnight at room temperature under argon. The mixture was concentrated to about 50 ml, filtered, and added to 800 ml of cold diethyl ether. The precipitated product was filtered and dried under reduced pressure. Yield 9.5 g. NMR (d6-DMSO): 2.53 ppm (t, —CH$_2$—COO—), 2.95 ppm (t, —CH$_2$-amine), 3.51 ppm (s, PEG backbone).

Example 9 illustrates the linking of a high molecular weight ("POLY$_A$") and low molecular weight ("POLY$_B$") polymer, by reaction of an amine on POLY$_B$ with a benzotriazole carbonate on POLY$_A$, to form a functionalized, segmented carbamate-linked polymer. In this case, the segmented polymer product has a carboxylic ester functionality (from the POLY$_B$ segment).

Example 9 mPEG(32 KDa)-propionic acid methyl ester

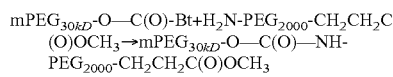

To a solution of mPEG(30 KDa)-benzotriazole carbonate (3.0 g, 0.1 mmol) (Shearwater Corporation) in methylene chloride (20 ml), PEG(2 KDa)-α-amino-ω-propionic acid methyl ester (the product of Example 8) (0.24 g, 0.12 mmol) and triethylamine (0.060 ml) were added, and the reaction mixture was stirred overnight at room temperature under argon. The mixture was filtered and the solvent was evaporated. The crude product was dissolved in methylene chloride, precipitated with isopropyl alcohol, and dried under reduced pressure. Yield 2.8 g. NMR (d$_6$-DMSO): 2.53 ppm (t, —CH$_2$—COO—), 3.11 ppm (q, —CH$_2$—NH—), 3.24 ppm (s, —OCH$_3$), 3.51 ppm (s, PEG backbone), 4.04 ppm (m, —CH$_2$—O(C=O)—), 7.11 ppm (t, —(C=O)—NH—).

Examples 10 and 11 demonstrate the conversion of the functional group, Y, of the segmented polymer produced in Example 9 from methyl propionate to propionic acid and propionic acid NHS ester, respectively.

Example 10 mPEG(32 KDa)-propionic acid

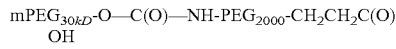

mPEG(32 KDa)-propionic acid methyl ester (the product of Example 9) (2.8 g, 0.082 mmol) was dissolved in 20 ml deionized water, and the pH was adjusted to 12.0 with 0.5 M NaOH solution. The reaction mixture was stirred 1.5 h at pH 12.0. Sodium chloride (3 g) was added, and the pH was adjusted to 3 with 5% phosphoric acid. The product was extracted with methylene chloride 3 times, and the combined extracts were dried with anhydrous magnesium chloride. The solvent was removed and the product dried under reduced pressure. Yield 1.6 g. NMR (d$_6$-DMSO): 2.44 ppm (t, —CH$_2$—COO—), 3.11 ppm (q, —CH$_2$—NH—), 3.24 ppm (s, —OCH$_3$), 3.51 ppm (s, PEG backbone), 4.04 ppm (m, —CH$_2$—O(C=O)—), 7.11 ppm (t, —(C=O)—NH—).

Anion exchange chromatography provided mPEG(32 KDa)-propionic acid (97.5%), Mpeg-30 KDa (2.5%).

Example 11 mPEG(32 KDa)-propionic acid, N-hydroxysuccinimide ester

To a solution of mPEG(32 KDa) propionic acid (product of Example 10) (1.6 g, 0.050 mmol) in anhydrous methylene chloride (10 ml), N-hydroxysuccinimide (0.0063 g, 0.055 mmol) was added, followed by 1,3-dicyclohexylcarbodiimide (1.0 M solution in methylene chloride, 0.05 ml, 0.055 mmol). The reaction mixture was stirred overnight at room temperature under argon, filtered, and concentrated. The crude product was dissolved in methylene chloride, precipitated with isopropyl alcohol, and dried under reduced pressure. Yield 0.9 g. NMR (d$_6$-DMSO): 2.81 ppm (s, —CH$_2$—CH$_2$— (succinate)), 2.92 ppm (t, —CH$_2$—COO—), 3.11 ppm (q, —CH$_2$—NH—), 3.24 ppm (s, —OCH$_3$), 3.51 ppm (s, PEG backbone), 4.03 ppm (m, —CH$_2$—O(C=O)—), 7.11 ppm (t, —(C=O)—NH—).

Example 12 illustrates the linking of a high molecular weight ("POLY$_A$") and low molecular weight ("POLY$_B$") polymer, by reaction of an amine on POLY$_B$ with a benzotriazole carbonate on POLY$_A$, to form a functionalized, segmented carbamate-linked polymer. In this case, the segmented polymer product has a butanoic acid functionality (from the POLY$_B$ segment).

Example 12 mPEG(23.4 KDa)-butanoic acid

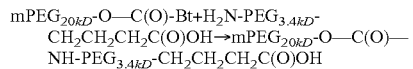

To a solution of mPEG(20 KDa)-benzotriazole carbonate (2.0 g, 0.1 mmol) (Shearwater Corporation) in methylene chloride (20 ml), PEG(3.4 KDa)-α-amino-ω-butanoic acid (0.45 g, 0.12 mmol) (Shearwater Corporation) and triethylamine (0.060 ml) were added, and the reaction mixture was stirred overnight at room temperature under argon atmosphere. The mixture was filtered and evaporated to dryness. The crude product was dissolved in methylene chloride, precipitated with isopropyl alcohol, and dried under reduced pressure. Yield 2.2 g. NMR (d$_6$-DMSO): 1.72 ppm (q, CH$_2$—CH$_2$—COO—) 2.24 ppm (t, —CH$_2$—COO—), 3.11 ppm (q, —CH$_2$—NH—), 3.24 ppm (s, —OCH$_3$), 3.51 ppm (s, PEG backbone), 4.04 ppm (m, —CH$_2$—O(C=O)—), 7.11 ppm (t, —(C=O)—NH—). Anion exchange chromatography yielded mPEG(23.4 KDa)-butanoic acid (92%), MPEG-20 KDa (8%).

Example 13 demonstrates the modification of the functional group, Y, of the segmented polymer produced in Example 12 from butanoic acid to butanoic acid N-hydroxysuccinimide ester.

Example 13 mPEG(22 KDa)-butanoic acid, N-hydroxysuccinimide ester

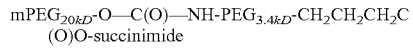

To a solution of mPEG(23.4 KDa)-butanoic acid (product of Example 12) (1.17 g, 0.050 mmol) in anhydrous methylene chloride (10 ml), N-hydroxysuccinimide (6.3 mg, 0.055 mmol) was added, followed by 1,3-dicyclohexylcarbodiimide (1.0 M solution in methylene chloride, 0.05 ml, 0.055 mmol). The reaction mixture was stirred overnight at room temperature under argon, filtered and evaporated to dryness. The crude product was dissolved in methylene chloride, precipitated with isopropyl alcohol, and dried under reduced pressure. Yield 1.0 g. NMR ($d_6$-DMSO): 1.83 ppm (q, $CH_2$—$CH_2$—COO—), 2.70 ppm (t, —$CH_2$—COO—), 2.81 ppm (s, —$CH_2$—$CH_2$-(succinate)), 2.92 ppm, 3.11 ppm (q, —$CH_2$—NH—), 3.24 ppm (s, —$OCH_3$), 3.51 ppm (s, PEG backbone), 4.03 ppm (m, —$CH_2$—O(C=O)—), 7.11 ppm (t, —(C=O)—NH—).

Examples 14A-C illustrate the linking of a medium- or high-molecular weight ("$POLY_A$") polymer and low molecular weight ("$POLY_B$") polymer (triethylene glycol diamine), by reaction of an amine on $POLY_B$ with a succinimide ester or benzotriazole carbonate on $POLY_A$, to form a functionalized, segmented carbamate-linked polymer. In this case, the segmented polymer product has an amine functionality (from the $POLY_B$ segment). Examples 14A and 14C illustrate preparation on a 200 g scale.

Example 14A mPEG(2 KDa) amine

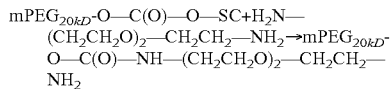

To a solution of 200 g (0.1 eq) of $mPEG_{2000}$ in 1 L acetonitrile was added 43.55 g (0.17 eq) disuccinimidyl carbonate. Upon dissolution, 24.4 ml anhydrous pyridine was added dropwise via syringe. The solution was then allowed to stir for 12 hours, filtered under argon, and concentrated to remove solvent. The residue was redissolved in 2 L dichloromethane, and the solution was washed with two 400 mL portions of 10% $NaH_2PO_4$: 25% NaCl. The aqueous extracts were back-extracted with 400 mL dichloromethane. The organic phase was combined, dried over sodium sulfate, filtered, and concentrated. This residue was taken up in 5 L of ether and stirred in a warm water bath under argon. Upon clarification the mixture was cooled in an ice bath, and the crystallized solid was filtered and dried under vacuum.

This product ($mPEG_{2000}$-succinimide) (206 g) was dissolved in 4.12 L dichloromethane. The solution was added dropwise with vigorous stirring, under argon, to a solution of 300 mL 2,2'-(ethylenedioxy)bis(ethylamine) ($H_2NCH_2CH_2OCH_2CH_2OCH_2CH_2NH_2$). The resulting solution was stirred for 12 h under argon, then concentrated under reduced pressure to give a viscous oil. This residue was taken up in a minimum amount of dichloromethane and precipitated by addition of 2 L isopropyl alcohol/2.5 L ether. The precipitated solid was filtered and dried under vacuum.

Example 14B mPEG(20 KDa) amine

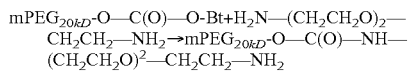

To a solution of mPEG(20 KDa)-benzotriazole carbonate (2.0 g, 0.1 mmol) (Shearwater Corporation) in methylene chloride (20 ml), 2,2'-(ethylenedioxy) bis(ethylamine) (MW 148.21, 0.3 g, 2.0 mmol) was added, and the reaction mixture was stirred 2 h at room temperature under argon. The solvent was evaporated to dryness, and the crude product was dissolved in methylene chloride and precipitated with isopropyl alcohol. The product was dried under reduced pressure. Yield 1.8 g. NMR ($d_6$-DMSO): 2.64 ppm (t, —$CH_2$-amine-), 3.11 ppm (q, —$CH_2$—NH—), 3.24 ppm (s, —$OCH_3$), 3.51 ppm (s, PEG backbone), 4.04 ppm (m, —$CH_2$—O(C=O)—), 7.11 ppm (t, —(C=O)—NH—). Cation exchange chromatography yielded mPEG(20K)-amine (97.5%).

Example 14C mPEG(20 KDa) amine

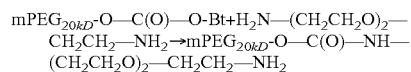

To 29.2 mL of 2,2-(ethylenedioxy)bis(ethylamine) was added, dropwise under argon via cannula, with vigorous stirring, a solution of 199.2 g mPEG(20 KDa)-benzotriazole carbonate and 0.4 g BHT in 4 L dichloromethane. The reaction mixture was allowed to stir overnight, and a sample was withdrawn to check the completeness of the reaction. The mixture was concentrated under reduced pressure, and the residue was taken up in a minimum amount of dichloromethane. The product was precipitated by adding 4 L of 1:1 isopropyl alcohol/ether and cooling in an ice bath. The product was filtered and washed with 3 L of ether to remove any excess reagent.

Example 15 demonstrates the conversion of the functional group of the low weight polymer, PEG(3.4 KDa)-α-hydroxy-ω-propionaldehyde, from a hydroxy to an amine group.

Example 15

PEG(3.4 KDa)-α-amine-ω-propionaldehyde diethyl acetal

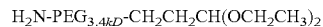

To a solution of PEG(3.4 KDa)-α-hydroxy-ω-propionaldehyde diethyl acetal (NOF Corporation, Tokyo, JP) (1.0 g, 0.294 mmol) in a mixture of toluene (20 ml) and dichloromethane (5 ml), triethylamine (0.07 ml, 0.502 mmol, 171% of stoichiometric amount) and methanesulfonyl chloride (0.028 ml, 0.362 mmol, 123% of stoichiometric amount) were added, and the resulting mixture was stirred overnight under nitrogen atmosphere. The mixture was filtered, and the solvent was distilled off under reduced pressure. The residue was added to a mixture of 16 ml concentrated $NH_4OH$ and 1.6 g $NH_4Cl$ and stirred 42 hours at room temperature. The reaction product was extracted with dichloromethane (3 times 20 ml). The extract was washed with 5 ml 1M HCl and 5 ml distilled water and dried with anhydrous sodium sulfate. The solvent was distilled under reduced pressure, giving 0.78 g of PEG(3.4 KDa)-α-amine hydrochloride-ωpropionaldehyde diethyl acetal. NMR ($d_6$-DMSO): 1.10 ppm (t, $CH_3$—, acetal), 1.74 ppm (q, —$OCH_2CH_2CH$—, acetal), 2.94 ppm (t, —$CH_2$-amine hydrochloride), 3.51 ppm (s, PEG backbone), 4.55 ppm (t, —CH—, acetal), 7.11 ppm (t, —(C=O)—NH—).

Example 16 demonstrates the linking of the low molecular weight ("POLY$_B$") polymer produced in Example 15, PEG (3.4 KDa)-α-amine-ω-propionaldehyde diethyl acetal, with a high molecular weight ("POLY$_B$") polymer, by reaction of an amine on POLY$_B$ with a benzotriazole carbonate on POLY$_A$, to form a functionalized, segmented carbamate-linked polymer. In this case, the segmented polymer product has a propionaldehyde diethyl acetal functionality (from the POLY$_B$ segment).

Example 16 mPEG(23.4 KDa)-propionaldehyde, diethyl acetal

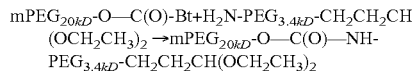

To a solution of mPEG(20 KDa)-benzotriazole carbonate (2.0 g, 0.1 mmol) (Shearwater Corporation) in methylene chloride (20 ml), PEG(3.4 KDa)-α-amine-ω-propionaldehyde diethyl acetal, the product of Example 15 (0.36 g, 0.106 mmol) was added, and the reaction mixture was stirred overnight at room temperature under argon atmosphere. The solvent was evaporated to dryness, and the crude product was dissolved in methylene chloride and precipitated with isopropyl alcohol. The precipitate was dried under reduced pressure. Yield 1.8 g. NMR (d$_6$-DMSO): 1.10 ppm (t, CH$_3$—, acetal), 1.74 ppm (q, —OCH$_2$CH$_2$CH—, acetal), 3.11 ppm (q, —CH$_2$—NH—), 3.24 ppm (s, —OCH$_3$), 3.51 ppm (s, PEG backbone), 4.04 ppm (m, —CH$_2$—O(C=O)—), 4.55 ppm (t, —CH—, acetal), 7.11 ppm (t, —(C=O)—NH—).

Example 17 demonstrates the conversion of the functional group, Y, of the segmented polymer produced in Example 16 from propionaldehyde diethyl acetal to propionaldehyde.

Example 17 mPEG(23.4 KDa)-propionaldehyde

mPEG(23.4 KDa)-propionaldehyde, diethyl acetal (product of Example 16) (1.8 g) was dissolved in 20 ml water, and the pH of the solution was adjusted to 3 with dilute phosphoric acid. The solution was stirred for 3 hours at room temperature, and 0.5M sodium hydroxide was added to adjust the pH of the solution to 7. The product was extracted with methylene chloride, the extract was dried with anhydrous magnesium sulfate, and the solvent was distilled off under reduced pressure. Yield: 1.6 g. NMR (d$_6$-DMSO): 2.60 ppm (dt, —OCH$_2$CH$_2$CH—, aldehyde), 3.24 ppm (q, —CH$_2$—NH—), 3.51 ppm (s, PEG backbone), 4.04 ppm (m, —CH$_2$—O(C=O)—), 7.11 ppm (t, —(C=O)—NH—), 9.65 ppm (t, —CH, aldehyde).

Example 18 demonstrates the linking of the low molecular weight ("POLY$_B$") polymer produced in Example 15 with a high molecular weight ("POLY$_B$") branched polymer, by reaction of an amine on POLY$_B$ with an NHS ester on POLY$_A$, to form a functionalized, segmented amide-linked polymer. The segmented polymer product has a propionaldehyde diethyl acetal functionality (from the POLY$_B$ segment).

Example 18

Branched PEG2(43.4 KDa)-propionaldehyde, diethyl acetal

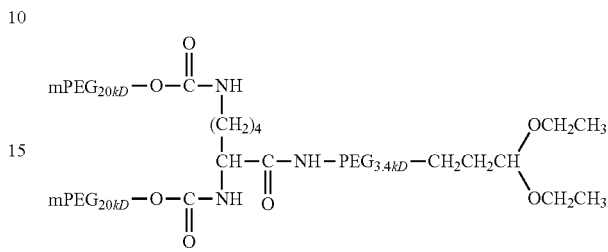

To a solution of branched PEG2 (40 KDa)-N-hydroxysuccinimide ester (1.0 g, 0.025 mmol) (Shearwater Corporation) in methylene chloride (8 ml), PEG$_{3.4\ KDa}$-α-amine hydrochloride-ω-propionaldehyde diethyl acetal (the product of Example 15) (0.12 g, 0.035 mmol) and triethylamine (0.01 ml) were added, and the reaction mixture was stirred overnight at room temperature under argon. The solvent was evaporated to dryness, and the crude product was dissolved in methylene chloride and precipitated with diethyl ether. The precipitate was dried under reduced pressure. Yield 0.83 g. NMR (d$_6$-DMSO):1.10 ppm (t, CH$_3$—, acetal), 1.74 ppm (q, —OCH$_2$CH$_2$CH—, acetal), 3.24 ppm (s, —OCH$_3$), 3.51 ppm (s, PEG backbone), 4.55 ppm (t, —CH—, acetal).

Example 19 demonstrates the conversion of the endgroup, Y, of the segmented polymer produced in Example 18 from propionaldehyde diethyl acetal to propionaldehyde.

Example 19

Branched PEG2(43.4 KDa)-propionaldehyde

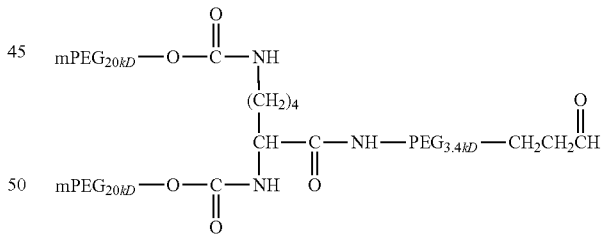

Branched PEG2(43.4 KDa)-propionaldehyde diethyl acetal (the product of Example 18) (0.4 g) was dissolved in 10 ml water, and the pH of the solution was adjusted to 3 with dilute phosphoric acid. The solution was stirred for 3 hours at room temperature, and 0.5M NaOH was added to adjust the pH of the solution to 7. The product was extracted with methylene chloride. The extract was dried with anhydrous magnesium sulfate and the solvent distilled off under reduced pressure. Yield 0.35 g. NMR (d$_6$-DMSO): 2.60 ppm (dt, —OCH$_2$CH$_2$CH—, aldehyde), 3.24 ppm (s, —OCH$_3$), 3.51 ppm (s, PEG backbone), 9.65 ppm (t, —CH, aldehyde).

Example 20 demonstrates the linking of a low molecular weight ("POLY$_B$") polymer with a high molecular weight ("POLY$_B$") polymer, by reaction of an amine on POLY$_B$ with a benzotriazole carbonate on POLY$_A$, to form a functionalized, segmented carbamate-linked polymer. In this case, the segmented polymer product has a maleimide functionality (from the POLY$_B$ segment).

Example 20

MPEG$_{20K}$-Maleimide

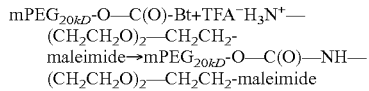

To a solution of mPEG(20 KDa)-benzotriazole carbonate (20.0 g, 0.001 mol) (Shearwater Corporation) in methylene chloride (200 ml), maleimide-triethyleneglycol-amine TFA (0.68 g, 0.002 mol) and 4-methylmorpholine (0.44 ml, 0.004 mol) were added. The reaction was stirred 4 hours at room temperature under argon. The solvent was evaporated to dryness and the product precipitated with isopropyl alcohol (1000 ml). The precipitate was collected by vacuum filtration and dried in vacuo overnight. Yield: 19.5 g. NMR (d6-DMSO): 3.11 ppm(q, —CH$_2$—NH—), 3.24 ppm (s, —OCH$_3$), 3.51 ppm (s, PEG backbone), 4.04 ppm (t,—CH$_2$—O(C=O)—), 7.04 (s, —(C=O)—CH=CH—(C=O)—), 7.11 ppm (t, —(C=O)—NH—).

What is claimed is:

1. A composition comprising (i) a pharmaceutical carrier and (ii) a conjugate of a water soluble polymer and a pharmacologically active agent, wherein the pharmacologically active agent is attached to the water soluble polymer via a functional group Y, wherein the water soluble polymer has a structure encompassed within the following formula:

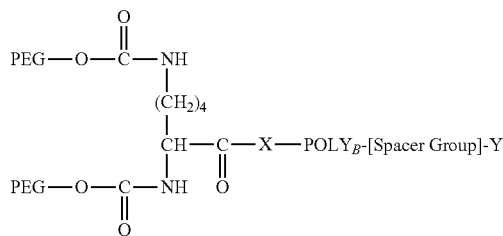

wherein:
each PEG is a poly(ethylene glycol) segment having a molecular weight ranged of from about 15000 to about 50000;
X is —NH—;
POLY$_B$ is a water soluble segment comprising 1 to about 120 monomeric units, which has a lower molecular weight than that of each PEG;
[Spacer Group] is a group linking Y to a terminus of POLY$_B$; and
Y is functional group.

2. The composition of claim 1, wherein POLY$_B$ comprises one monomer or up to three different monomers selected from the group consisting of alkylene glycol, olefinic alcohol, vinylpyrrolidone, hydroxyalkylmethacrylamide, hydroxyalkylmethacrylate, saccharide, α-hydroxy acid, phosphazene, oxazoline, and N-acryloylmorpholine.

3. The composition of claim 1, wherein the molecular weight of each PEG is at least twice that of POLY$_B$.

4. The composition of claim 1, wherein POLY$_B$ comprises at least 2 monomeric units.

5. The composition of claim 1, wherein POLY$_B$ is a poly(alkylene glycol) segment.

6. The composition of claim 5, wherein POLY$_B$ is a poly(ethylene glycol) segment.

7. The composition of claim 1, wherein POLY$_B$ is poly(ethylene glycol) segment having a molecular weight selected from the group consisting of about 88, about 132, about 176 and about 220.

8. The composition of claim 1, wherein the Spacer Group is a hydrolytically stable group.

9. The composition of claim 1, wherein the Spacer Group is a hydrocarbon spacer.

10. The composition of claim 9, wherein the hydrocarbon spacer is a linear divalent alkyl chain.

11. The composition of claim 10, wherein the linear divalent alkyl chain has 4 to about 8 carbons.

12. The composition of claim 1, wherein Y is a nucleophilic group.

13. The composition of claim 12, wherein Y is selected from the group consisting of hydroxyl, amine, hydrazine, hydrazide and thiol.

14. The composition of claim 1, wherein Y is an electrophilic group.

15. The composition of claim 14, wherein the electrophilic group is selected from the group consisting of carboxylic acid, carboxylic ester, imide ester, orthoester, carbonate, isocyanate, isothiocyanate, aldehyde, ketone, thione, alkenyl, acrylate, methacrylate, acrylamide, sulfone, maleimide, disulfide, iodo, epoxy, sulfonate, thiosulfonate, silane, alkoxysilane, halosilane and phosphoramidate.

16. The composition of claim 15, wherein the electrophilic group is a carboxylic acid.

17. The composition of claim 15, wherein the electrophilic group is a carboxylic ester.

18. The composition of claim 15, wherein the electrophilic group is an aldehyde.

19. The composition of claim 15, wherein the electrophilic group is a maleimide.

20. The composition of claim 1, wherein the each PEG is end-capped with a capping group selected from the group consisting of C$_1$-C$_{20}$ alkoxy, C$_1$-C$_{20}$ aryloxy and a phospholipid.

21. The composition of claim 20, wherein the capping group is C$_1$-C$_5$ alkoxy.

22. The composition of claim 21, wherein the capping group is methoxy.

* * * * *